US012667734B1

(12) United States Patent
Steele

(10) Patent No.: US 12,667,734 B1
(45) Date of Patent: Jun. 30, 2026

(54) PERSONAL PORTABLE SYSTEM TO RAPIDLY COLLECT AND REMOVE ELECTROMAGNETIC RADIATION AND EXTRANEOUS MAGNETIC AND VOLTAGE FIELDS FROM A HUMAN BRAIN AND BODY, AND PROMOTE HEALING BY RAPID REDUCTION OF TISSUE OXIDATIVE STRESS AND INFLAMMATION PROCESSES

(71) Applicant: Diane Michelle Steele, Chevy Chase, MD (US)

(72) Inventor: Diane Michelle Steele, Chevy Chase, MD (US)

( * ) Notice: Subject to any disclaimer, the term of this patent is extended or adjusted under 35 U.S.C. 154(b) by 347 days.

(21) Appl. No.: 17/740,108

(22) Filed: May 9, 2022

(51) Int. Cl.
　　*A61N 2/06*　　　(2006.01)
　　*A61N 1/14*　　　(2006.01)

(52) U.S. Cl.
　　CPC ................. *A61N 2/06* (2013.01); *A61N 1/14* (2013.01)

(58) Field of Classification Search
　　CPC .................................... A61N 2/06; A61N 1/14
　　See application file for complete search history.

(56) References Cited

U.S. PATENT DOCUMENTS

| | | | | |
|---|---|---|---|---|
| 383,177 | A | * | 5/1888 | Greene et al. .......... B28B 7/183 |
| | | | | 249/74 |
| 2,350,534 | A | * | 6/1944 | Rosinger ............. A47J 43/0465 |
| | | | | 310/104 |
| 6,683,779 | B2 | | 1/2004 | Ober |
| 7,724,491 | B2 | | 5/2010 | Ober et al. |

| | | | | |
|---|---|---|---|---|
| 2008/0199824 | A1 | * | 8/2008 | Hargadon ............... A61F 5/566 |
| | | | | 433/6 |
| 2013/0072787 | A1 | * | 3/2013 | Wallace ................. A61B 90/50 |
| | | | | 600/424 |
| 2017/0229692 | A1 | * | 8/2017 | Thiel ................... H01M 50/271 |
| 2018/0141011 | A1 | * | 5/2018 | Mou ..................... B01F 33/452 |

(Continued)

FOREIGN PATENT DOCUMENTS

| | | | | |
|---|---|---|---|---|
| WO | | WO006218 | 1/2008 | |
| WO | | WO-2008006218 A1 | * 1/2008 | ............... A61N 2/02 |

OTHER PUBLICATIONS

V&P Scientific's multi bottle stirring system. https://www.youtube.com/watch?v=cDD-FAns26U. published Nov. 19, 2015. Accessed Feb. 28, 2025. (Year: 2015).*

*Primary Examiner* — Carrie R Dorna
*Assistant Examiner* — Joshua D Lannu

(57) ABSTRACT

A personal system to collect and remove electromagnetic radiation (EMR) and excess magnetic and voltage fields from a human body includes portable and non-portable embodiments that, when applied to skin, can causes EMR fields to be drawn out of the body toward a magnet before which the wave is split into separate electrical and the magnetic fields at the surface of the containers. Extraneous magnetic fields coming from the body are absorbed into the magnetic field of the internal magnet while simultaneously donating electrons and creating electrical current within the body to reduce oxidative stress inflammation. A portable handheld system includes a fanny/back pack, a revised standard insulated conductive grounding cord and a specialized cap for mobile use of standard grounding equipment. The system includes more high-powered non-portable similarly functioning EMR-removing vacuum-like booster instruments and protective wearable outer gear.

18 Claims, 11 Drawing Sheets

(56) References Cited

U.S. PATENT DOCUMENTS

2019/0133602 A1* 5/2019 Kiemeneij ......... A61B 17/1325
2020/0038654 A1* 2/2020 Doskocil ................ A61B 5/202
2020/0391925 A1* 12/2020 Marantis ............... A61J 1/1412

* cited by examiner

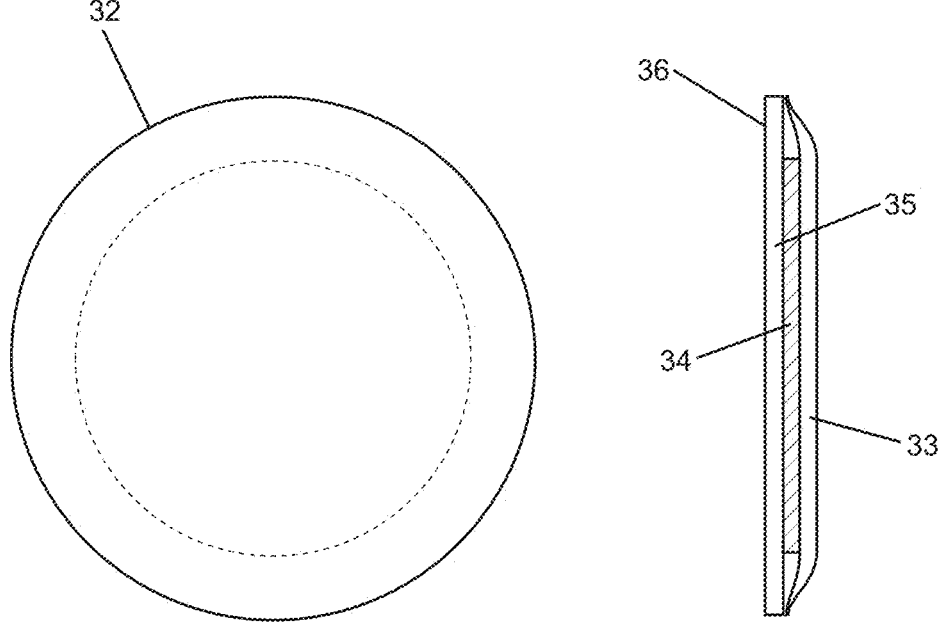
FIG. 4                    FIG. 5

63
64
65

57    56

42

66

PERSONAL PORTABLE SYSTEM TO RAPIDLY COLLECT AND REMOVE ELECTROMAGNETIC RADIATION AND EXTRANEOUS MAGNETIC AND VOLTAGE FIELDS FROM A HUMAN BRAIN AND BODY, AND PROMOTE HEALING BY RAPID REDUCTION OF TISSUE OXIDATIVE STRESS AND INFLAMMATION PROCESSES

CROSS REFERENCE TO RELATED APPLICATION

This application claims priority from provisional patent application No. 63/235,339, titled, "Therapeutic Magnetic and Electromagnetic Radiation Splitter," filed Aug. 20, 2021.

BACKGROUND OF THE INVENTION

1 Field of the Invention

The present invention relates generally to the fields of electromagnetic radiation (EMR), its harmful effects in the body, Havana Syndrome, oxidative stress and inflammation, the healing processes and benefits of earth-grounding, magnetic therapy, and electrical stimulation therapy; and particularly to a personal therapeutic electromagnetic radiation-removal system to collect and remove electromagnetic radiation, excess voltage and/or magnetic fields, and reduce oxidative stress and inflammation from a human body.

It is generally known that the electromagnetic spectrum, from the lowest to the highest frequency (also known as the longest to the shortest wavelength), includes radio waves (radio, television, radar), microwaves, infrared radiation, visible light, ultraviolet radiation, X-rays, and gamma-rays. EMR is produced whenever electricity is used to power something. In EMR energy, its two-component waves—electrical and magnetic—travel through space together inseparably, propagating each other readily as they travel because its electrical current produce magnetic fields and its magnetic fields produce electrical current as they move. Everyday sources of EMR include by X-rays, MRI's, CT scans, cell towers, drones, satellites, satellite stations, TV, Wi-Fi routers, computers, cellphones, power lines, smart meters, microwaves, appliances, tanning beds, welding torches, blow dryers, possibly electric cars, and the like. The more voltage that enters an electrically powered object, the greater the EMR field that is generated. Regular exposure to these sources of EMR has become fairly typical in recent years, and health consequences have been documented.

The World Health Organization/International Agency for Research on Cancer, has classified radio frequency (such as is emitted by cell phones), as group 2B which is reserved for carcinogens and shared by lead and pesticides. In a review of the research, Levellos (1995), noted a correlation between. EMR exposure and leukemia in children in several studies, while others have found a connection between EMR exposure and various neurological, psychiatric and endocrine problems along with blood changes such as decreased serum antioxidants and psychiatric disorders which included, "sleep disturbances, dizziness, difficulties with memory recall and concentration, headache, depression, dysesthesia, and others." (Tasalloti, 2021). Additional research commonly cites symptoms of EMR exposure to include: tissue oxidative stress, inflammation, nausea, shakiness, tinnitus, and other nervous system, and cognitive impairments. In a study of rats subjected to EMR for one hour per day for 2 months, authors concluded, "EMR exposure caused structural changes in the frontal cortex, brainstem and cerebellum and impaired the oxidative stress and inflammatory cytokine system. This deterioration can [lead] to disease including the loss of these areas' function and cancer development," (Eser, et. al.). It is also known that, "the brain is prone to oxidative damage because of its high metabolic activity and high vulnerability to ischemic damage. Oxidative stress and inflammation (OSI) thus, plays a major role in the pathophysiology of both acute and chronic pathologies in the brain, such as stroke, traumatic brain injury or neurodegenerative diseases," Matyas (2021).

Beyond the effects of expected EMR exposure levels, a constellation of cognitive and neurological damages resulting from unexpected catastrophic exposure from unknown sources, began to surface among American diplomats stationed in Cuba in 2016 (The National Academies of Sciences, and many others). Since then, the symptoms and immediate causes of the neurologic injuries have been studied extensively by the U.S. Government (Williams, K., Herb, J., 2021; CNN, and many other organizations), and they are described as cognitive dysfunctions similar to traumatic brain injury (TBI). The group of TBI-like cognitive dysfunctions was named "Anomalous Health Incidents (AHI)," or "Havana Syndrome," and shortly thereafter, the Help American Victims Afflicted by Neurological Attacks (HAVANA) Act of 2021 became law to provide healthcare for those affected (Public Law 117-4 (10/08/2021). U.S. authorities have determined that the most likely cause of these TBI's is highly focused pulsed EMR (CNN, and many others), that is being directed at targets both inside their homes and while out in public. Weapons of this sort are called directed-energy weapons (DEWs), and include pain rays, lasers, masers, microwaves, particle beams, ultrasonics, sound beams, etc. DEWs are used by various military groups (Department of Defense, Popular Mechanics, Fox News, and many others.). Further, if the body and/or brain become magnetized, however temporary, DEWs waves hitting around the same time can penetrate even deeper into the body and/or brain due to the pull of the internal magnetic environment.

As of 2022, the incidence of Havana Syndrome is no longer limited to U.S. diplomats to Cuba (The National Academy of Sciences, et., al.). Reports of neurological attacks on government officials also come from Europe, Asia, Latin America, Canada, and the streets of Washington, DC. (The National Academies of Sciences, et., al.). Inside the U.S., targets now include officials in other branches of the Federal government as well as American citizens in the general civilian population (Griffin, 2021, 60-Minutes, February 2022, and many others). Use of the neuro-warfare technology is on the rise, and in the wrong hands it is not unlikely that, in addition to attacks causing cognitive destruction, an individual's thought process, including visual and auditory processes could be tapped into and interrupted or otherwise tampered with for purposes of espionage. Altogether, clandestine neurological warfare using microwave and other DEWs is a matter of national security and the negative health effects of EMR exposure can be severe. A means to treat and remediate the intrusive and destructive effects of egregious EMR exposure in the human brain and body is clearly needed.

As previously mentioned, exposure to microwave radiation (or EMR), can produce oxidative stress and inflammation (OSI), which is a primary contributor to the disease process (Chauhan, 2017), including brain damage (Eser, et. al.). If, however, antioxidants capable of donating electrons are either present (occurring naturally in the body), or supplementally introduced into the OSI process, oxidative stress and the damage it causes can be decreased and neutralized and, in some cases, repaired (Oschman, et. al.), (Eser, et. al.) (Matyas, 2021) (Shcharbina (2021), depending on treatment timing and exposure levels (Matya, 2021). It is well known that OSI arises as a result of having too many immune-system generated free radicals (atoms that are missing an electron) (Chauhan, 2017, et. al.). This happens when the body's natural immune response goes "too far" and excess free radicals begin to steal electrons from healthy cells. Otherwise healthy cells start to oxidize and become damaged at their surface or inside the cell wall where important cellular mechanisms including DNA operate (Matyas, Oschman, et. al.). Saygin (2015), studied two groups of young rats exposed to EMR, with one group simultaneously supplemented with the antioxidant Gallic (from black tea), and found that the supplemented group suffered significantly less inflammation and oxidative damage. It would be beneficial in the treatment of catastrophic EMR-exposure, and even lesser exposure levels, to include electron donation provisions as needed and there are several ways to do so.

OSI-reducing antioxidants, with their supply of donatable free electrons, are conveyed to us by eating a diet that is rich in a variety of fruits and vegetables. There also is a sizeable market for antioxidant supplements such as Glutathione and CoQ10, among others, which are extremely powerful electron donors. Xia, J., (et. al., 2016), found that the antioxidant curcumin, found in turmeric, increased blood flow and reduced hypertension in the rat brain's microcirculatory system, an essential goal in OSI reduction. Magnesium sulfate, when administered to stroke patients, worked to enhance the antioxidant benefits of Glutathione and was found to provide neuroprotection and repair free radicle damage to the blood-brain-barrier and neutralize free radicle damage of brain cells, resulting in significantly less neurological and cognitive damage and impairment than standard treatment (Matyas, 2021). Shcharbina (2021) found that magnesium sulfate administration to stroke patients significantly decreased the dysfunction of blood-brain barrier (p<0.009) with 93% of those under standard therapy continuing to exhibit blood-brain barrier dysfunction afterward, compared to 41% who received standard therapy plus magnesium sulfate supplementation. However, antioxidant therapy is sometimes considered ineffective because the consequences of oxidative stress can be severe and the optimal dose for antioxidant therapy has not been agreed upon (Matyas, 2021). Additional and alternative electron donor sources are also available.

One popular source of free electrons comes from physical connection to the earth's surface which has an abundant and limitless supply that can be utilized by the body as needed to meet the needs of circulating free radicals—if the skin comes into contact with it (Ober, May 25, 2010). This process is called, "earthing" or "grounding." Ober, Sinatra and Zucker have shown that earth-grounding reduces oxidative stress and acute or chronic inflammation by decoupling blood cells to thin the blood which speeds up the healing process by increasing the ability of the blood to carry oxygen and nutrients to an injury site, carry toxins away from the site more quickly, and to beneficially reduce the overall cytokine (inflammatory) process. The way it does this is by electron donation that produces a greater negative charge on the surface of the blood cells (zeta potential) which causes the cells to repel one another (Ober, et. al.). Additionally, the process of earth-grounding removes excess voltage from the body, whether acquired by EMR exposure, electric fields, radio frequencies, etc. Excess voltage in the body has been found to interfere with normal cellular communications and contribute to the immune system disease process (Ober, 2004). Unfortunately, it is not always possible to connect directly to the earth with bare skin. As a result, earth-grounding gear was developed to be used indoors.

Indoor-based earth-grounding equipment comes in the form of conductive pads, mats, seat pads, bands, blankets, pillowcases, sheets, patches and more, and was designed to remove excess voltage from the body. While proven highly effective (Ober, et. al.), the equipment used to achieve these beneficial anti-inflammatory results requires the user to remain stationary while using them because a conductive connection from the piece of equipment to the earth or to the third prong in a standard grounded electrical outlet is required, which keeps the user tethered to the immediate area. Further, equipment-based earth-grounding is a passive means of adding electrons to the body and removing excess voltage and is not designed to remove heavy levels of EMR or excess magnetic field from the body or brain. As such, this equipment may be more useful for everyday exposure than for high-level acute or chronic exposure from focused high-energy microwave and other EMR attack weapon scenarios such as those that result in Havana Syndrome. In the high-exposure high-OSI scenario, time is of the essence. The faster the offending elements can be removed and dispensed with, the quicker the OSI and the damage (including brain damage), it causes can be interrupted and reversed.

One means to remove excess magnetic field from the body is through the use of magnets. Magnet therapy or magnetotherapy has been around for thousands of years, and is used mainly to reduce pain and inflammation and promote healing from injury, and which is now known to achieve "analgesia across a broad range of different types of pain neuropathic, inflammatory, musculoskeletal, fibromyalgic, rheumatic, and postsurgical." (Eccles, 2005)—also an object of the instant invention. However, the mechanisms behind how this is accomplished have not been fully agreed upon. One practitioner (Bansal, H. L., 1976), specifies that when a static magnet is placed on the skin, magnetic flux (the perpetually moving rotational north to south flow of magnetic fields, see FIGS. 3 and 14), passes through tissue (which has its own magnetic field and chemically based electrical currents), creates another electrical current along the natural flux lines of the magnet (magnetism in motion creates electrical current), and increases the electrical conductivity of blood cells, which causes them to repel one another and flow more efficiently. Similarly, a sodium ion solution is added by blood banks to keep red blood cells decoupled. At-home magnetotherapy equipment comes in the form of bracelets, insoles, neck braces, knee bands, pillows, blankets, discs, etc., while in-office practitioners generally use bare magnet arrays. Causing more efficient healthier blood flow to aid and producing free electrons in the process of electrical current generation in injury healing may help explain why bare magnet bracelets work somewhat even when they aren't fastened to an injury site. The standard strength used in magnetotherapy is 400-4,000 Gauss (Souder, 2021), and effectiveness depends on the polarities used, flux vector configurations, and severity of injury. A typical N45 neodymium quadrapolar 1.12"×0.25' disk magnet, with a flux plate to concentrate the magnetic field, is said to penetrate up to 50 mm or 2 inches into the tissue (Q™ Magnets). However, the average human head is 6 to 7 inches wide and 8 to 9 inches long. Quadrapole magnets or multiple magnetic arrays are also more effective in the healing process than standard magnets because flux lines of mixed polarity or other arrays of magnets are stronger and can penetrate more deeply (or more broadly), than a single dipole magnet (Souder, 2021). Though effective for use on the body, a 5 cm flux line depth would not be enough to effectively treat whole-brain EMR. Further, any EMR being removed by a bare magnet would create additional EMR when voltage comes in contact with the magnet. All of these shortcomings could be remedied by using stronger, protected, and grounded magnets.

Another type of magnet therapy is called repetitive transcranial magnetic stimulation (rTMS) (Sorokina, 2018), which directs electrical energy via a magnetic field to specific areas of the brain by having a metal object coiled with copper wire and pulsed with electricity along the copper whereby the electrical current is enabled through the magnetic field to enter the brain and stimulate targeted nerve cells. While this form of therapy is used to treat a variety of brain-based disorders such as, depression, anxiety, and other mental disorders, it is used only when other therapies fail (Mayo Clinic, 2018). Still, it is useful knowledge for the background of the current invention, to know that magnetic flux fields easily penetrate the skull and blood-brain barrier which is notoriously difficult to accomplish (Kong, et. al. 2012). The ability of magnetic fields to penetrate into the brain is an important consideration in the treatment of TBI, as from Havana Syndrome, because high-powered EMR exposure typically affects the brain since the brain acts as an antenna for it (Schamiloglu). Also important is that the studies at NIMH (2018) reported the magnetic field used in rTMS are about the same as an MRI machine in strength (5,000-30,000 gauss), and can reach 2 inches inside the brain. Using stronger but permanent magnets and creating various magnetic flux field juxtapositions could further the depth and breadth that magnetic flux fields can penetrate the brain, and, if these magnet-based apparatus were also able to collect and discard excess voltage as well, it could solve the magnet-only or earth-grounding-only treatment impasse for treatment of extreme-level EMR exposure.

Finally, it is within the scope of the present invention to offer the practical hypothesis that the beneficial effects of antioxidant supplementation, earth-grounding, and permanent magnet therapy, are all achieved in a manner similar to that of a fourth widely used pain and inflammation therapy called electrical stimulation (e-stim) therapy. E-stim therapy is used by medical professionals such as chiropractors, physical therapists, and many others, for the purpose of reducing pain and chronic inflammation caused by injury. In the field of e-stim, minor electrical impulses are delivered to tissues (such as the low back), which reportedly reduces pain and OSI by causing targeted muscles to repeatedly contract and therefore blood flow to increase as a result (Roland, 2019). However, the electrical currents used are also creating magnetic field, donating electrons, and creating a greater negative charge on the surface of blood cells which enables them to de-couple and flow more freely. In all four therapies, (antioxidant supplementation, earth-grounding, magnet therapy, and e-stim), it can be reasonably deduced that an in-common OSI-reduction mechanism is the creation of electrical current in targeted tissue and the donation of free electrons, which together creates a blood cell negative charge and results in thinning of the blood for a more oxygenated nutrient-rich flow and more efficient removal of toxins that result from the inflammation process. The present invention fulfills these same therapeutic OSI-reduction essentials while concurrently removing deep EMR, deep magnetic fields and nodules, and excess voltage. (Magnetic nodules are created anywhere in the body with repeated targeting using DEW weapons such as pain rays. These may be similar to trigger points which are muscular knots that cut off their own blood supply.)

By definition, rapid and timely EMR overload elimination reduces exposure time and OSI period—both known to increase the probability of experiencing more severe health problems, including severe cognitive decline and cancer. A system that safely, portably, rapidly, and proactively removes deep EMR and excess magnetic and voltage fields, and relieves OSI is possible, beneficial, and needed. Such a therapeutic system should also be user-friendly and portable. The instant invention fulfills these needs.

2 Description of the Related Art

Devices have been disclosed in the prior art that relate to a process called earth-grounding, the use of therapeutic magnets to heal injury and reduce inflammation, electromagnetic therapy, and e-stim for the easing of aches and pains, healing, and helping alleviate mental disorders. Some include devices that have been patented, and generally relate to removal of excess voltage and/or pain relief and OSI reduction, having particular elements that diverge from the present invention. The following is a list of devices deemed most relevant to the present disclosure, which are herein described for the purpose of highlighting and differentiating the unique aspects of the present invention, and further highlighting the drawbacks existing in the prior art.

U.S. Pat. No. 6,683,779 B2 (2004) to Ober discloses a personal conductive earth-grounding mat (or seat pad, band, or patch) that when pressed to the human body and connected to the earth, collects and removes excess voltage from the body and adds free electrons to the body in the process. The commonly used 2-layer mat is composed of carbon fibers in an outer layer, a dissipative foam underlayer, a conductive snap attached to conductive cord at a first end and with a metal rod that is designed to be placed into the earth at a second end. While disclosing a novel and effective electron adding and voltage removal earth-grounding system, the Ober device relies on passive removal of the polluting elements over time and is not readily portable because it requires a conductive cord that tethers the user to the ground. In addition, while the device removes voltage effectively and adds electrons naturally, it does not have the capability of removing excess magnetic field or magnetic nodules from the body.

In one embodiment, the instant invention employs a 3-layer conductive/dissipative/conductive grounding mat with embedded magnets that can be used as a grounding mat when conductive grounding cords are employed appropriately. EMR waves, both voltage and magnetic components, are actively removed from the body in this manner: the EMR waves attract to the magnets in the mat and carry the voltage with it, and while the magnetic field of the EMR wave combines with the flux fields of the magnet, the voltage portion of the EMR wave splits off at the surface of the mat due to the conductive properties of the mat and cord. In another embodiment, the 3-layer mat (without internal magnets), can be conformed into a fanny/back pack designed to carry magnet-based handheld EMR-removers inside the casing. In both embodiments, inflammation is reduced by creating free electrons inside tissue and creating a negative surface charge to blood cells using the electrical current generated by the pure magnetic flux fields. It is worth noting that for the purposes of the current invention, it is unsafe to leave the dissipative side of the conductive mat exposed in a heavy EMR environment because it becomes saturated with the environmental EMR which overloads the overall voltage drainage system and brings removal of body voltage to a standstill, perhaps flowing into the body instead of out depending on the respective concentration levels of the EMR. In another embodiment, the instant invention makes use of a standard 2-layer conductive/dissipative mat that encloses a stronger heavy-duty non-portable magnet arrangement, with or without an attached metal dish to serve as at least one flux plate for redirecting and deepening magnetic flux for more thorough EMR removal. In another mat embodiment of the instant invention, there is a smaller non-groundable flexible conductive bottom layer with adhesive, a flexible polyurethane inner layer that may or may not contain an aqueous solution or hydrocolloidal substance, and a flexible non-conductive plastic outer layer.

U.S. Pat. No. 7,724,491 B2 (2007) to Ober discloses a process leading to the reduction of body tissue inflammation by providing a conductive pad upon which an individual would rest their bare feet and which is connected to a conductive cord that is staked into the earth. This process reduces the oxidative stress response of the body that produces inflammation by drawing the free electrons that hover upon the earth's surface to the body and grounding excess bodily voltage into the earth. While disclosing the natural process by which the body is able to gain electrons from the earth's surface to make up for free radical electron deficits, the device requires the user to stay in one place while using it because it necessarily makes use of a conductive cord that must be pressed into the earth. Nor does the Ober device have the capacity to remove the magnetic component of EMR from the body. In addition, the Ober device specifies a dissipative layer of the specified 2-layer grounding mat to be partly exposed. In the instant invention the dissipative layer of the 3-layer mat is not exposed to the environment in any embodiment. There also is a portable magnet-based component to the current invention that makes a magnet-based 3-layer mat and other standard grounding equipment (e.g., patch, car seat mat, band, etc.), portable for the removal of EMR.

U.S. Patent WO 2008/006218 A1 to C. G. Air Systems, Inc. (International, except U.S.) and to Ciechanowski (U.S. only), discloses magnetotherapy systems designed for use in a variety of open-ended water-bearing tubs such as bathtubs and whirlpools, etc. that employ magnetic fields propagated by electromagnets such that when positioned near key points on the human body perform either soothing/relaxing or calming/anti-inflammatory measures. Therapeutic benefits discussed include also increased circulation of the blood and lymph fluids, stimulation of nerve impulses, and increases in production of the hormone endorphin which reduces pain. Electromagnets, made up of conductive wire wrapped around a piece of metal such as iron, are affixed to the outer and/or underside of a tub and the user is provided with a means to increase or decrease the magnetic field to be distributed within the water of the tub by adjusting the amount of electricity that circulates through the coil. Presumably, the voltage does not cross the tub barrier. An advantage of using an electromagnet over a permanent magnet is that the strength of the magnetic field can easily be adjusted by changing the flow of the electrical current. However, the advantage of using a fully bounded rare earth magnet, which can also provide varying levels of stimulation depending on array and orientation, is that it can remove EMR from the body because it makes use of an actual magnet which has the ability to attract outside magnetic fields and so is not comprised only of flux lines being sent into the body as from an electromagnet. Lastly, the instant invention with similar properties, is portable in several embodiments.

U.S. Patent 2021/0170189 to Souder discloses a reconfigurable array of high-powered magnets for use by practitioners in the field of magnet therapy. The device allows the practitioner to efficiently manipulate a variety of magnetic field configurations depending on the whether the practitioner prefers to cause the magnetic flux to penetrate broadly or deeply or in multiple sites simultaneously with like or mixed polarities. The devices are enclosed in cloth wraps, presumably for sanitation and patient comfort. While in a normal setting these devices may be well-suited to their purposes, in high-EMR-exposure scenarios, such as in the cases of Havana Syndrome, Souder's device would allow the voltage component of the EMR wave to make contact with the magnet and thus propagate EMR rather than remove it.

Q™ Magnets retails therapeutic quadrapolar magnets encased in plastic as some individuals are allergic to the magnet coatings (gold, nickel), and to preserve colored stickers. The company also retails magnet filled blankets, as do other magnetotherapy companies. These products differ from the instant invention in that the magnets are not double-protected from conducting voltage by being surrounded by distilled water inside the plastic coating, and the blankets, etc., are not groundable. In fact, sleeping with a cloth blanket embedded with magnets would attract high-level EMR waves and propagate the deleterious waves.

It is the object of the present invention to provide safe, strong, protected, portable and non-portable, groundable, and effective whole-body, EMR-wave removal products that can actively and deeply collect and remove heavy loads of noxious EMR as well as any extraneous magnetic and/or voltage field when applied to a human body and/or brain by separating the EMR wave into its constituent components and disposing of any electrical current while making use of the magnetic fields. Further, that the present system be able to reduce OSI by creating strong, voltage-free, pure magnetic flux fields that donate free antioxidizing electrons and create biological electrical current inside blood and body tissue to promote development of negative blood cell surface charge to enhance blood flow, oxygenate, and aid the transport of nutrition needed for more rapid healing of harmed body tissues, especially in the highly metabolic brain, and to aid the nervous system by removing EMR and improving blood oxygenation.

A further object of the current EMR-removal system is that at least one light-weight device be provided that can be carried by hand or worn hands-free on the body using a specialized and optionally groundable pack and be able to be applied to the body in a variety of therapeutic ways to remove EMR and decrease OSI.

Another object is to provide a means to perform standard magnet therapy using interchangeable mixed pole arrays by joining portable handhelds together in varying patterns, magnets spaced apart because of the width of their containers.

Another objective is to provide a means to use a standard grounding patch, mat, seat, band, etc. portably by providing a modified straight-pronged conductive cord that can be inserted into a specialized cap of a handheld at one end and conductively connected to a standard piece of grounding equipment using a snap at another end, and which then serves as a transportable EMR-removal mechanism.

Another objective is to enhance the means of portability for the handheld EMR-remover by providing a 3-layer mat that can be used alone or be fashioned into a fanny-back pack designed to contain one or more handhelds—preferably a duo. Buckle-together straps allow the user to carry the handhelds in a variety of therapeutic ways—as a fanny pack, or, when stepped into while on a floor with the belt furthest away from the feet, then straps raised up behind the neck and crossing over the front shoulders, becomes a back pack (which can be raised or lowered by tightening or loosening the belt). The pack also has a conductive snap for connecting to a grounded outlet when used indoors.

Another objective is to provide a 3-layer mat-like embodiment comprised of a non-groundable flexible nonconductive plastic or latex-free bottom layer with adhesive, a flexible inner layer of a foil-like, mylar-like, or other reflective material, and a flexible non-conductive plastic or latex-free outer layer. The objective is to provide a protective covering that serves as blocker to keep EMR from entering the body wherever it is affixed.

A further objective is to extend the utility of standard electrostatic grounding mats and earth-grounding mats and improve their ability to remove EMR from the body and brain by providing one or more magnets sealed inside such a mat in a manner that assures that the dissipative layer is on the innermost side and not in any part exposed, and which, when supplied together with a conductive snap and conductive cord system can more rapidly remove heavy EMR loads, and excess voltage and magnetic fields from anywhere on the body with which it comes into contact. This mat, when grounded properly, can be hung over the back of a chair with the lower magnet spanning the area just underneath the shoulder blades and the other end rolled into a neck-rest or extended over the head for protection and therapy. It can be laid across or under the body while sleeping, or rest across the hips or under the feet. The speed with which EMR etc., is removed from the body is enhanced by the magnets inside.

Another object of the current EMR-removal system is to provide a higher-powered means for EMR-removal, by using a series of strong magnets and optionally attaching a metal flux plate dish to the magnet series to redirect and deepen the flux fields. This embodiment may or may not include a wedge with an appropriate indent for tilting the dish for more comfortable use on the forehead or base of the skull, or any area where deep and/or broad EMR removal is needed and comfort is desired. The non-dish end serves to pull deep location-focused EMR out while the vacuum-like metal dish side serves to pull deep in a broader area. There also may or may not be a magnet ring around the closed end of the dish to enhance the therapy by complicating the flux lines. The best uses for this equipment include sleeping with one or more near the head. The enhanced depth and breadth ensures deep brain flux penetration.

The above objects have been achieved in the form of prototypes of the various embodiments of the instant invention that have been developed and used by the inventor for more than five years to eliminate the effects of systematic high-level exposure to magnetic fields, electrical fields, and to egregious doses of high-level EMR from a variety of military-grade EMR weaponry systems in use by domestic terrorists as a means for harassment for which an FBI has been opened. Both simple and sophisticated science-based techniques for optimal use have also been developed and employed with great success as the inventor ethically serves as her own study subject.

SUMMARY OF THE INVENTION

The present invention is provided having portable and non-portable components to an EMR-removal/OSI-reduction system that collects and removes EMR from a human body by first having a non-conductive insulative adsorbent container filled with distilled insulative non-conductive water that surrounds a powerful rustproof-coated magnet. There is a plastic cylindrical 3-4 oz. container with a cap containing a 3"×½" bar-style N52 neodymium magnet coated in epoxy and filled with distilled water. When a "handheld" is applied to scalp or skin, the device causes EMR magnetic and electrical fields to be magnetically drawn out of the body toward the magnet to be split into separate electrical and magnetic fields at the surface of the insulative adsorbent handheld container and on contact with the distilled water. Removed voltage hovers on the outside of the plastic housing and passively dissipates voltage into the environment. Further, distilled water inside the container has no free ions to allow for conduction of electricity so no voltage from the EMR wave can travel with the magnetic field at that point to further propagate the wave by hitting the magnet, reinforcing the voltage blocking effects of the plastic container. An epoxy coating on the magnet further ensures a clean magnetic-field-only internal environment. The magnetic fields of the EMR wave, on the other hand, because there is no way to shield magnetic fields (one can only redirect), are provided a low impedance path to the internal magnet to which it is readily attracted. The magnetic field from EMR is simply absorbed into the magnetic field of the internal magnet, beneficially strengthening the field. When applied to the skin, magnetic flux lines generated by the internal magnet enter the body tissue or bone. Once inside the tissue, the flux lines stimulate secondary electrical currents that serve to increase the negative surface charge of blood cells which causes them to repel one another and decouple. The decoupling enhances the flow of blood and increases its oxygen and nutrient carrying capabilities and the ability to carry toxins away to be cleansed by the organs. Free electrons are donated in the electrical conduction process. As a result, EMR is reduced in the body or brain, the flow of blood increases, electrons are donated, and OSI begins to be reversed. Powerful magnets used on the brain would not disrupt the magnetic fields that naturally reside in the body because as long as atomic-level electrons keep moving, they will continue to generate their own tiny magnetic fields.

In the above embodiment there is a standard cap and a specialized cap with a rubber port on its topside. Caps are provided for filling and replacing the handheld with distilled water. If an electric field happens to penetrate the plastic container, water molecules separate into hydrogen and oxygen gases ("water-splitting"), which reduces the water level and may leave the magnet exposed to voltage or EMR waves. In the preferred embodiment two handhelds may be connected to one another via magnetic attraction to form a handheld duo. The duos can be held in the hands which are natural earth-grounding outlets of the body because of their many nerve endings, or applied anywhere on the body. Places include forehead, top of the head, chin, sternum, ribs, abdomen, hip bones, lower back, shoulders, under the feet (which also have numerous nerve endings), pinned to the body via clothing (e.g., inside the waistband of pants, the knee area inside leggings, etc.), back of the neck, along the spinal cord, low back, along major nervous and circulatory pathways, such as the vagus nerve and main aortic pathways. When used on the ears (with same-pole on each), for example, the device duo also helps prevent EMR radiofrequencies from entering the brain via the ear canal as well as help to drain EMR from the auditory nervous system. A fanny/back pack to transport the handheld duo is provided and includes a male snap mechanism for optional grounding, a means for closing a top flap to secure the contents, and a buckle-together set of straps for hands-free transport. The handheld duo inside the pack can be worn in the low-back, hip, abdominal areas like a fanny pack, or along the back like a backpack.

In a preferred embodiment, two handheld duos, each with standard or specialized caps, are connected together via the attraction of opposing magnetic fields. The mixed polarity flux fields created in this embodiment are complex, whether formed into a block with space in between duos, whether formed into an L-shape (e.g., to wear behind the neck/shoulder area), or connected end to end. It is generally known that quadrupole magnets are superior to standard magnets in that they lead to deeper penetration of the flux fields and more effective healing when used to reduce pain and inflammation.

In another embodiment, the utility of both the handheld or handheld duo, as described above, is extended by connecting to and a standard grounding patch is extended by providing a portable patch-grounding system that includes a modified standard conductive cord that need not be plugged into an earth-grounding medium such as the earth or the third prong in a standard wall outlet. Instead, the prong end is inserted into the inner magnet area of a handheld container by way of a specialized cap with a port that accepts, in a leakproof manner, a modified straight prong end of an otherwise standard insulated conductive cord. The other end of the modified straight prong conductive cord is comprised of a standard female snap arrangement that connects to any standard earth-grounding apparatus including a grounding patch, mat, car seat, blanket, pillow, body bands, etc., thereby enabling mobilization of that grounding equipment. If a handheld duo is used, the cord need only enter one of the handhelds to provide an effective means of portable grounding, The apparatus may be used with a 3-layer grounding mat configured into a fanny/back pack.

In a 3-layer mat-like embodiment, is a non-conductive non-grounding snap-less protective covering that, when attached to the body via suitable flexible adhesive, blocks EMR from entering the body at the point at which it is placed. This is very useful against the abuse of pain ray devices with their pinpoint accuracy. This embodiment is not limited to a flat patch but can be form-shaped to slip over a toe or finger or wherever an attack is destructively repetitive. In a preferred embodiment, when the patch adheres to the skin, the inner layer of foil-like, mylar-like, or other reflective internal material, is not exposed to the environment in any portion but is covered top and bottom by a flexible plastic or rubber material layer. There are no limitations as to the shape or form of the patch which could include an ability to fit over a toe, or come in the shape of a hat (another plastic layer takes the place of the adhesive), for example.

In another EMR-removing embodiment, magnets may be encased in a protective container that is composed of either a 1-layer conductive mat, a 2-layer conductive/dissipative mat, or a 3-layer conductive/dissipative/conductive electrostatic grounding mat, so long as the conductive carbon infused layer is outermost and no inner dissipative layers remain exposed. It includes a standard male snap configuration that conductively penetrates all layers used and is connected to an insulated conductive grounding cord at one end and attached conductively to the third prong of an electrical outlet or to a series of handheld duos at its other end. While bodily or environmental EMR's may enter the encasement, the voltage separates from the EMR wave by being conductively removed, while the magnetic waves are absorbed into the magnetic fields of the enclosed magnet array, leaving a constant pure magnetic flux to enter the body while pulling excess magnetic field out of the body. The preferred embodiment of the mat includes 2 sets of 8 block magnets anchoring each end of the then sealed grounding mat. Different magnet arrays, alternative ways of inserting the magnets, and different sized mats are also envisioned. These mats may be sat upon, wrapped around the body, laid over the head and/or down the back of a chair, and used as blankets.

In another embodiment, less-portable more powerful and heavier magnets are enclosed in a 2-layer dissipative/conductive material conductively connected to a standard insulated conductive grounding cord and plugged into a grounded outlet. This powerful configuration attracts deep EMR waves, separates the electrical waves from the magnetic waves using the conductive material layers, snap, and grounding cord while the magnetic waves are absorbed into the magnetic fields of the enclosed N52 array. These larger units are designed for deeper EMR removal, such as in the skull, brain, brainstem, jaw, hips, and knees. The preferred embodiment is constructed of 4 approximately 1½" W×2¼" L N52 block magnets with standard nickel or other coating connected to one another by magnetic attraction. The assembly of magnets is enclosed by a standard 2-layer electrostatic dissipative/conductive or 3-layer conductive/dissipative/conductive grounding mat, so long as the conductive carbon infused layer is outermost. It includes a standard male snap configuration that conductively penetrates all layers used and is connected to an insulated conductive grounding cord at one end and attached conductively to the third prong of an electrical outlet at the other end. The ends of the unit are used for focused, deep pull of EMR out of the body and concurrent flux line distribution into the tissue. A handheld duo may be attached to each end for added strength and flux field diversity and depth and breadth of removal.

In another embodiment, the less-portable larger device includes a shallow metal dish connected at its base to either end of the N52 body. The dish serves to redirect the magnetic flux field to elongate, strengthen, and broaden the magnetic pull without having to add magnets, bulk or weight to the embodiment, and to provide a cupping comfort when used on the head or body. The non-dish end of the magnet array may be used for focused, deeper pull and deep flux line penetration. A conductive wedge-shaped metal object, with or without an indent for a sturdy fit with the dish, can be attached in between the magnet and the dish to cause the dish to be fixed at a tilt. When sealed inside a 2-layer grounding mat, it can be used behind the head at the base of the skull, along the rounded forehead, cack of head, the chest, jawline, or any other area on the body. Other configurations include reducing or increasing the number of internal magnets and connecting, by magnetic attraction, a handheld duo to the non-dish end, and/or using multiple smaller dishes. The dish may or may not have a magnetic ring encircling the dish at its base.

Other objects, features, and advantages of the present invention will become apparent from the description taken in conjunction with accompanying drawings and claims.

BRIEF DESCRIPTION OF THE DRAWINGS

Although the characteristic features of this invention will be particularly pointed out in the claims, the invention itself and the manner by which it may be made and used may be better understood after a review of the following description, taken in connection with the accompanying drawings wherein like numeral annotations are provided throughout.

FIG. 4 shows a top view of the non-conductive protective covering.

FIG. 5 shows a side view of the non-conductive protective covering illustrating the material layers with the optional adhesive or snap components.

DETAILED DESCRIPTION OF THE INVENTION

Figure 1:
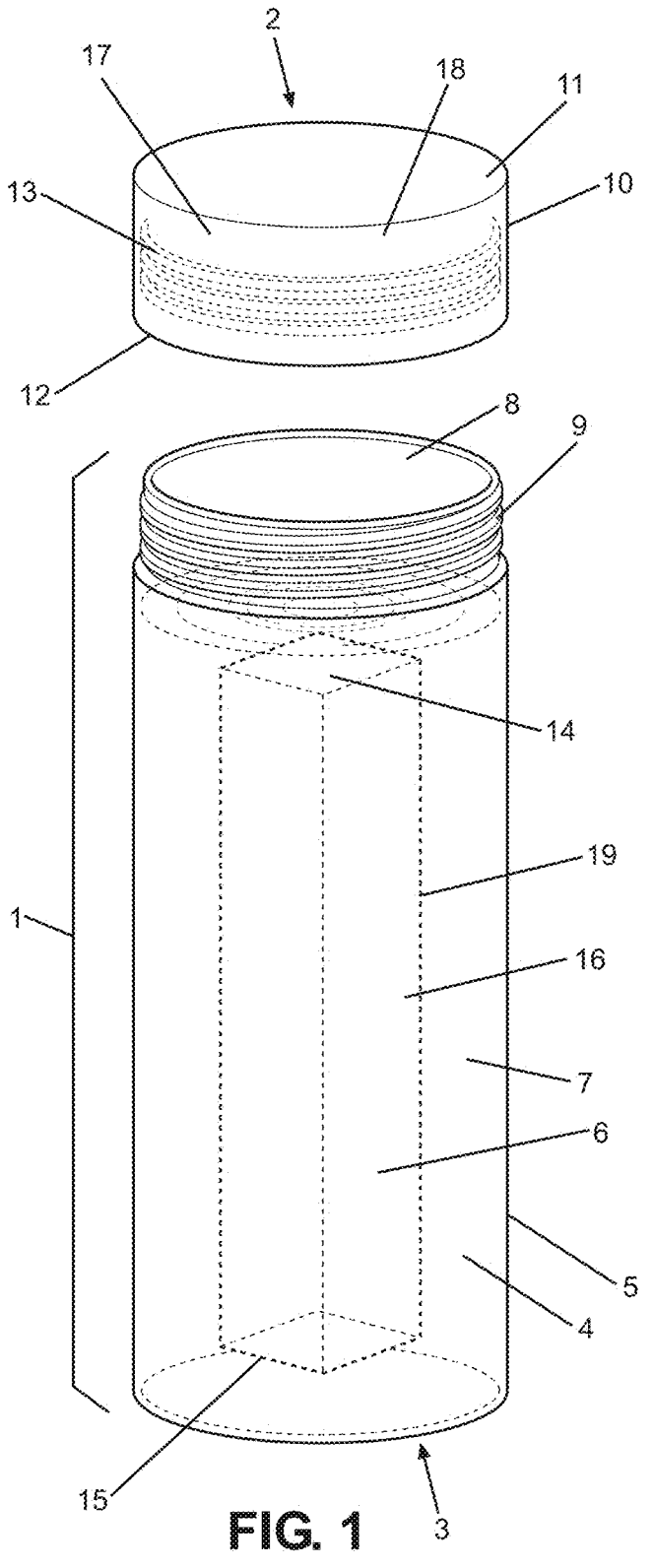
FIG. 1 shows a perspective side view of the central body of the handheld device with a standard cap and a magnet within it submerged in distilled water.

Reference is made herein to the attached drawings. Like reference numerals are used throughout the drawings to depict like or similar elements of the personal therapeutic neuro-warfare counter-terrorism system.

For the purposes of presenting a brief and clear description of the present invention, the preferred embodiments will be discussed as used for providing the user with an EMR-removal system having the capability for extracting EMR from the body and rendering the radiation energy harmless in the process together with the means to transport one of the devices conveniently and easily. The present invention is ideally suited for use in geographic areas where neuro-warfare is a risk or even where public or private equipment emits EMR on a regular basis, such as from cell phones, power lines, remote electrical panels, electric cars and the like. The figures are intended for representative purposes only and should not be considered to be limiting in any respect.

Referring now to FIG. 1, there is shown a perspective cross-sectional view of the elements of the present invention that work in conjunction with one another to form the body of the therapeutic handheld EMR-removing device. In the preferred embodiment there is a central body of the handheld (1) with a top end of the handheld (2) and a bottom end of the handheld (3) and a central body inside (4) and a central body outside (5). The central body of the handheld can take on many shapes though the preferred shape is cylindrical for handheld comfort. The preferred material is plastic which acts as an insulator of electrical energy and as an electrostatic dissipative substance. The central body of the handheld is of sufficient size to hold at least one magnet (6) and to hold enough fluid (7) in the central body inside (4) so that it can envelop the magnet (6) in its entirety. The top end of the handheld (2) has a port (8) for exchanging old fluid for fresh fluid as needed. The preferred fluid is distilled water because it is not a conductor of electricity. The port (8) comprises the top end of the handheld (2). Also at the top of the central body are outer threads of the central body (9) or other means able to secure a cap or lid to prevent the contents from spilling out. A standard cap (10) with a cap top end (11) and a cap bottom end (12) and a standard cap inside (17) and a standard cap outside (18) and secures onto the outer threads of central body (9) to prevent the fluid from leaking out. The standard cap inside (17) inner threads (13) and connects to outer threads of central body (9). The standard cap, when secured to the central body of the handheld (1) is preferably equal in circumference with the central body. Alternatively, the cap (10) could have outer threads and the central body (1) could have the inner threads rather. There is a top end of the magnet (14) and a bottom end of the magnet (15) and at least one side surface of the magnet (16), and a rustproof coating (19). The preferred magnet (6) is a block-style 4-sided rust proof epoxy coated N52 neodymium magnet. The rare earth N52 magnets are the strongest permanent magnets in the world, exert a continuous strength, and even small sizes have high performance pull strength. The preferred magnet (6) measures about 3 inches in length and ½ inch width on all 4 sides. The central body and the cap are preferably made from an insulating material such as PET plastic which measures about 4" in height and holds approximately 4 oz. of distilled water.

Figure 2:
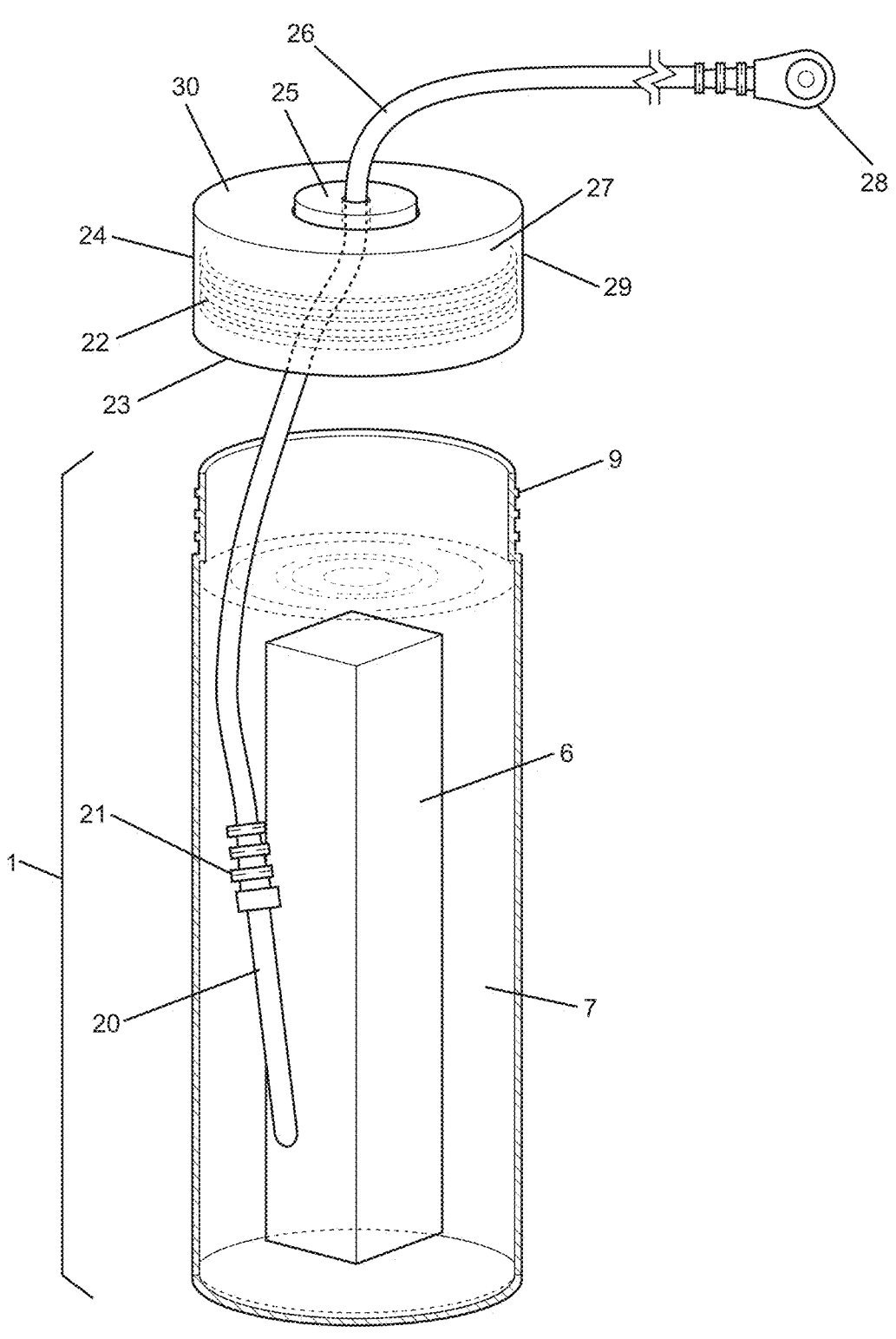
FIG. 2 shows a perspective side view of the central body of the handheld device with a modified cap, a rubber stopper port and a modified conductive straight-prong attached to a standard insulated conductive grounding cord with a standard conductive standard female conductive snap mechanism end. The modified grounding cord is shown inserted into the central body of the handheld and the straight prong dangles in the water near the magnet, perhaps attached to it.

FIG. 2 shows a perspective cross sectional view of the handheld with an accessory cap (24), the magnet (6), submerged in fluid (7), and the straight metal prong (20) which is inserted into the rubber stopper port (25) on the top end of the accessory cap (30). The straight metal prong (20) is connected to a standard insulated conductive grounding cord (26) which leads to a standard female snap end (28). The standard female snap end (28) connects to the male snap of any compatible piece of grounding equipment (mat, patch, chair, sock, glove, pillow, etc.). There may or may not be at least one resistor and/or diode (21) connected inside the standard insulated conductive grounding cord (26). There is a top end of the accessory cap (30), a bottom end of the accessory cap (23), an inside of the accessory cap (27), and an outside of the accessory cap (29). The bottom end of the accessory cap (23) inside of the accessory cap (27) may have inner threads of the accessory cap (22) for connecting the accessory cap (24) to the central body of the handheld (1).

Figure 3:
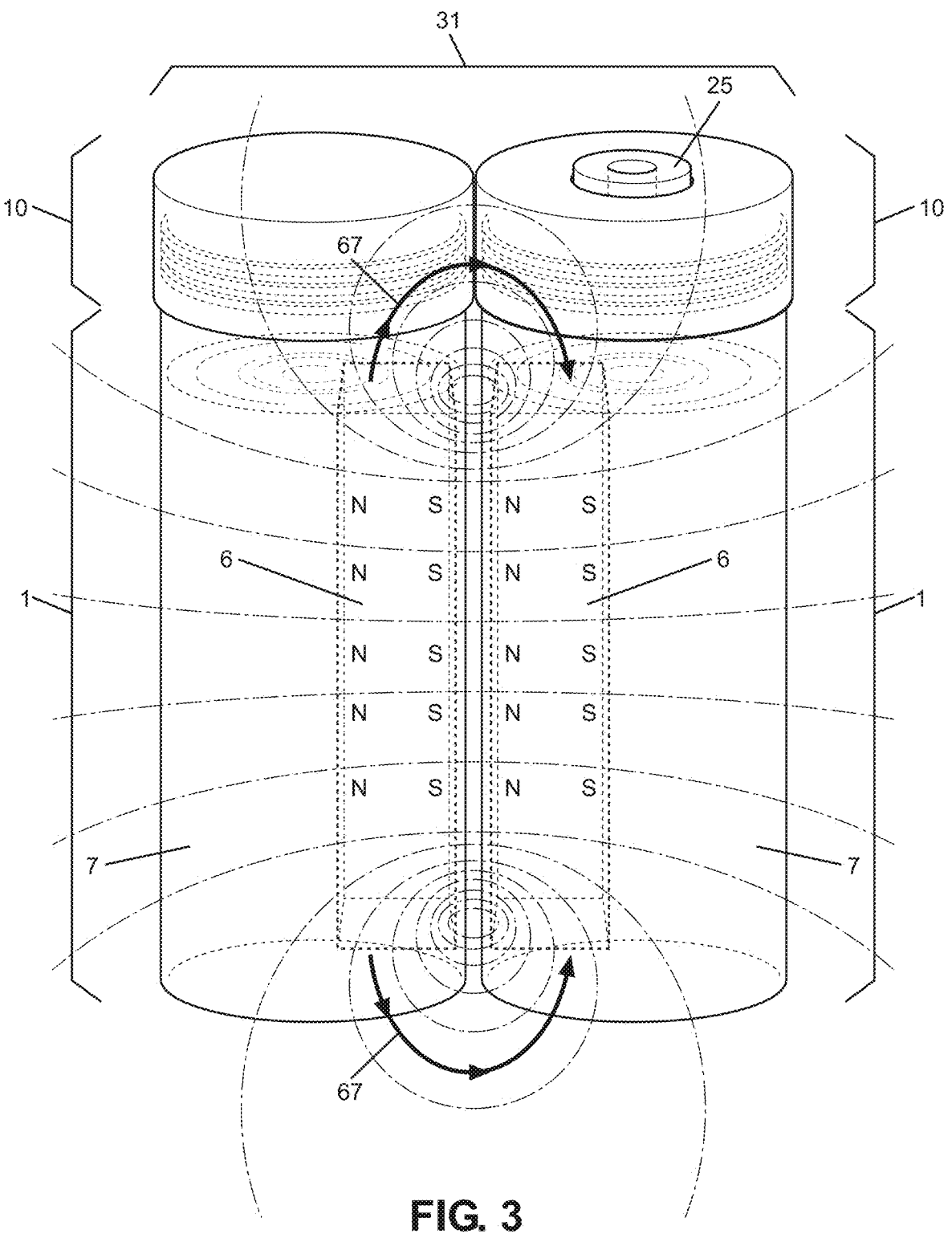
FIG. 3 shows a perspective side view of two handhelds connected to one another and illustrating theoretically the magnetic North (N) South(S) flux fields.

FIG. 3 shows a perspective side view of the device of FIG. 1, connected to a second such device to create a handheld duo (31) and illustrating theoretically the magnetic North (N) South(S) flux fields (67).

FIG. 4 is a top view of a non-conductive protective patch topside (32).

FIG. 5 is a cross-sectional side view of the layers of the non-conductive protective patch (32). The top layer is a flexible plastic or rubber top layer (33). The protective patch middle layer is an mylar or shiny foil-like layer (34) with the shiny side facing toward the top layer. The protective patch (32) has a bottom layer (35) that is also a flexible plastic or rubber with a skin-friendly adhesive (36) facing away from the middle layer (34) for attaching to the skin.

Figure 6:
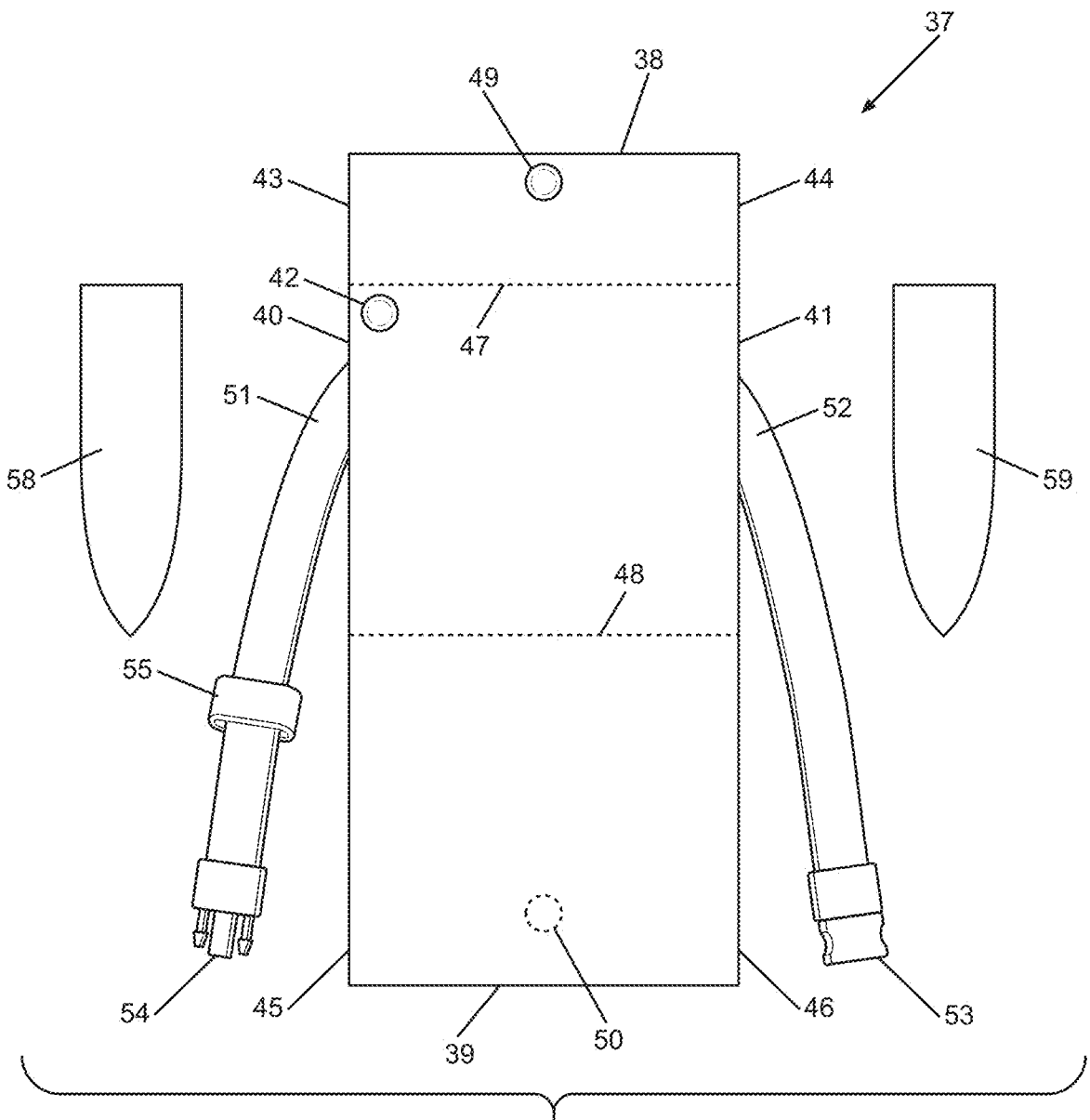
FIG. 6 shows a top view of the inside of the 3-layer mat with a penetrating male snap mechanism to be conformed into a fanny-back pack, with the pack components.

FIG. 6 is a top view of the a 3-layer grounding mat to be constructed as the inside of a fanny/back pack (37). In its simplest form, the pack (37) is configured to fit and to fully encompass a handheld duo (FIG. 3(31)). The pack (37) has a top edge of the pack (38), a bottom edge of the pack (39), a fold 1 (47) and a fold 2 (48). There is a left-side edge of the pack (40) and a right-side edge of the pack (41). Peripherally located on the left side is a male conductive snap mechanism (42) that penetrates all layers of the material to which it is. The male conductive snap mechanism (42) can be located elsewhere as determined desirable. The pack (37) as shown is folded along fold 1 (47) to create a closing flap (see also FIG. 8). Fold 2 (48) allows the left-side edge (40) to be sewn or otherwise securely connected to the lower left-side edge (45). Similarly, the right-side edge (41) connects with the lower right-side edge (46). The upper left edge (43) and the upper right edge (44), remain unconnected so that the section of material there can be used as a flap. There is an inner flap clasp mechanism (49) to be secured as needed to an outside outer flap clasp mechanism (50). (See also FIG. 8.) Material panels (58) and (59), when sewn along the side edges of the pack body (37), can be used to create more interior space. When not to be made into a pack, the 3-layer grounding mat can be any size and be embedded with one or more magnets and used as a grounding mat.

Figure 7:
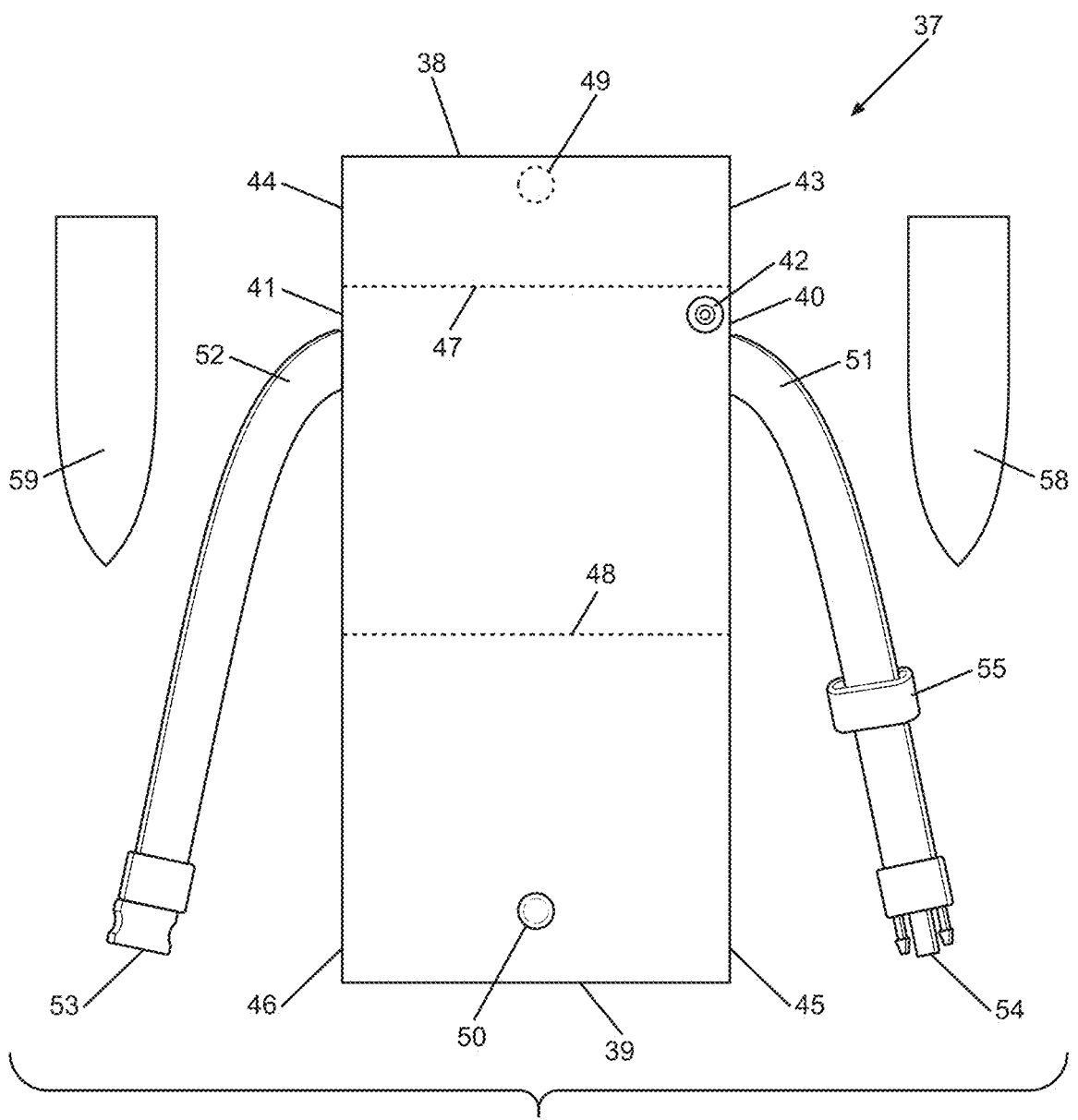
FIG. 7 shows a top view of the outside of the 3-layer mat with a penetrating male snap mechanism to be conformed into a fanny-back pack, with the pack components.

FIG. 7 is a top view of the 3-layer grounding mat of FIG. 6 to be constructed as the outside of the pack (37). Near the upper left edge, below fold 1 (47), is attached a female side belt strap (51). Attached near the upper right edge, below fold 1 (47) is a male side belt strap (52). The far end of the female side belt strap (51) is attached a female clasp mechanism (53). Similarly, the far end of the male side belt strap is comprised a male clasp mechanism (54). The female and male clasps mechanisms are standard plastic fanny pack clasps wherein the male clasp (54) fits securely inside the female clasp (53) to form a secure connection. There is a belt loop (55) located along the male side belt strap (52) to contain excess strap tail. The male conductive snap mechanism (42) is shown on the upper right side of the pack material. When folded, the outer flap clasp mechanism (50) connects securely to the inner clasp mechanism (49). Material panels (58) and (59), when sewn along the side edges of the pack body (37), can be used to create more interior space.

Figure 8:
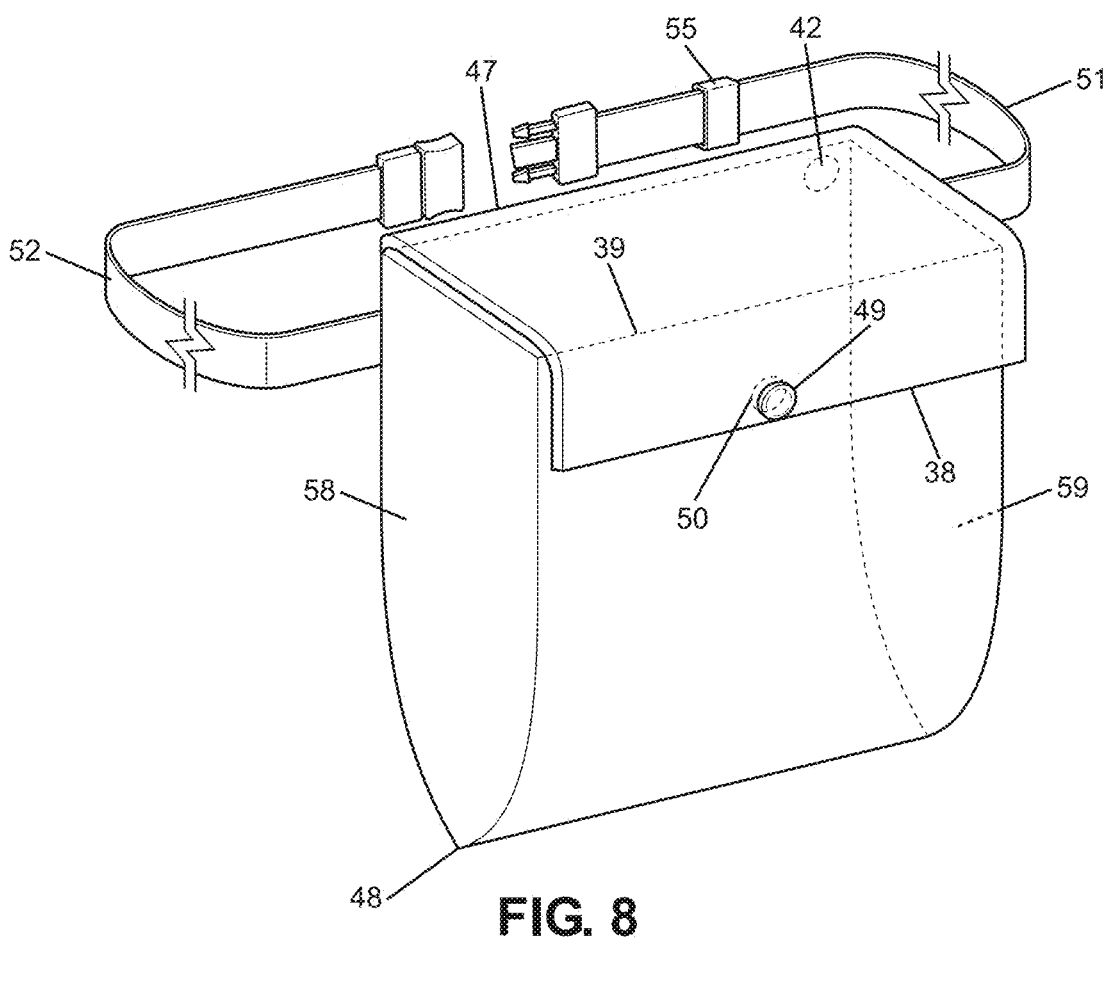
FIG. 8 shows a perspective side view of the folded fanny-back pack and components.

FIG. 8 is a perspective view of the folded pack. Fold 1 (47) creates the lid-like flap, while fold 2 (48) creates the carrying area for the handhelds. Material panels (58) and (59) may be connected to the lower side edges to create more space or the edges can be sewn together directly. Located on the underside of the flap and centrally located near the top edge (38) is the inner clasp (49). The inner clasp is designed to securely connect to the outer clasp (50) which is located centrally near the bottom edge (39). Alternatively, the top of the pack may be secured by a plastic hidden zipper (not shown). The male snap mechanism (42) is shown on the upper back side of the pack. Shown also here is the female belt strap (51) and the male belt strap (52), and the belt loop (55).

Figure 9:
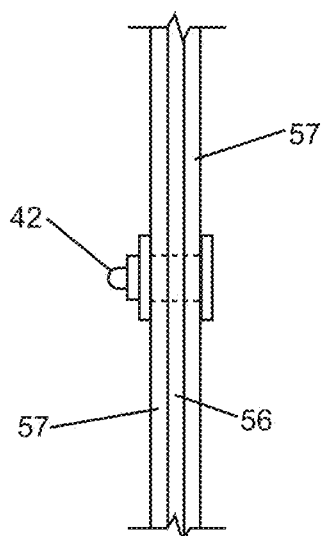
FIG. 9 shows an enlarged cross-sectional view of the mat/fanny-back pack material layers and penetrating male snap mechanism.

FIG. 9 is a cross-sectional view of the 3 layers of the preferred material that the pack (37) or any sized grounding mat may be made of. The layers are not the same as standard electrostatic style grounding mats. There is an inner electrostatic dissipative layer (56), and two carbon infused outer conductive layers (57) that protect and sandwich the inner electrostatic dissipative layer (54). There is a conductive male snap mechanism (42) penetrating all layers of the material. Magnets may be embedded in the dissipative layer. When used to create a pack (37) the covering may be also comprised only one layer of material (i.e., conductive (carbon-infused) only or insulative (plastic) only). In its simplest form, the pack (37) is configured to fit and to encompass the central body and caps of one or more handhelds, and may be configured to carry straight-prong grounding cords and grounding patches. The preferred configuration is two handhelds (31, FIG. 3) per pack (37). When used as a mat in conjunction with a grounded insulated grounding cord, it is configured to not actively over-absorb ambient EMR into the dissipative layer and instead, absorb mostly that which comes from the body tissue it touches.

Figure 10:
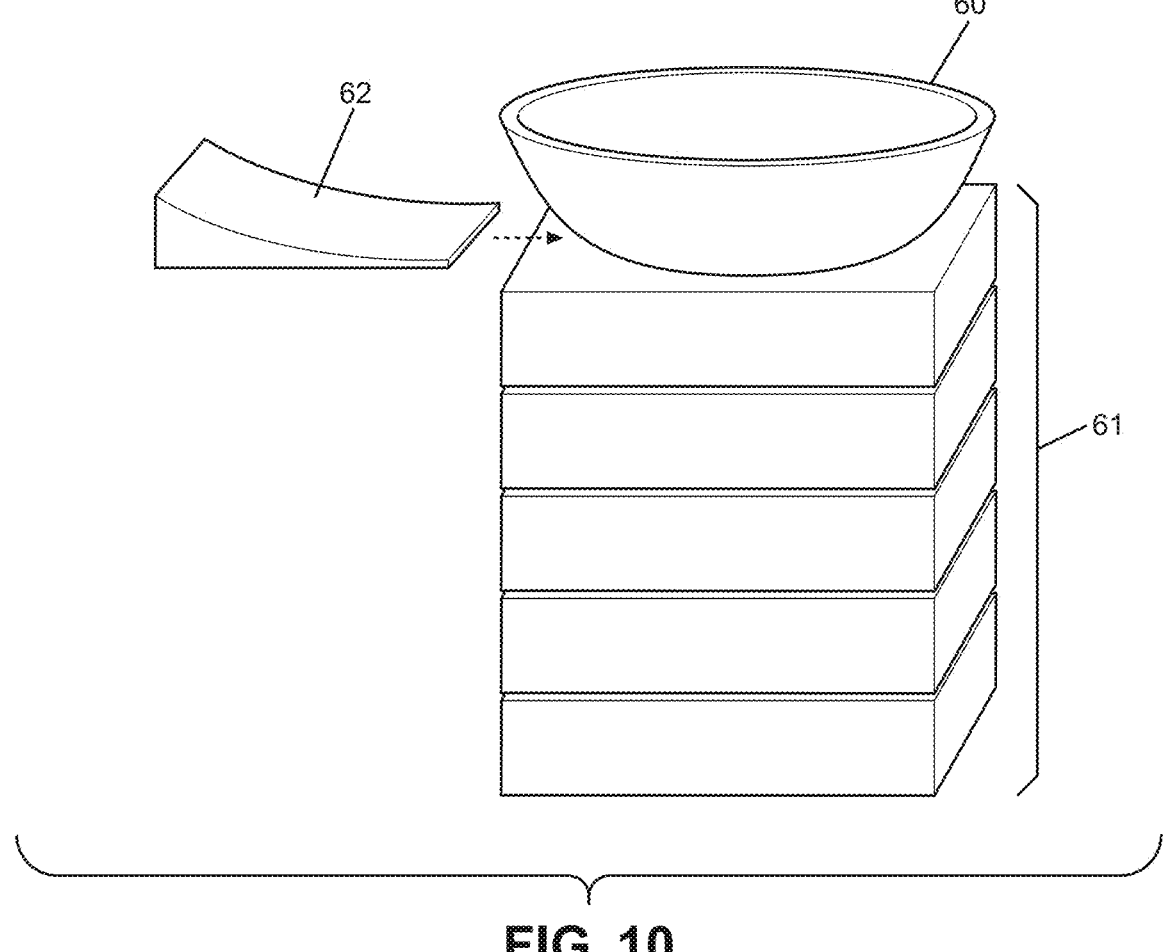
FIG. 10 is a perspective view of a number of magnets attached to a metal dish and a wedge.

FIG. 10 is a perspective side view of a metal dish (60) magnetically attached to an N52 magnet body (61) that is comprised of several large N52 magnets that are attached to one another by magnetic attraction. A metal wedge (62) may be shaped for solid insertion between the magnet body (61) and the metal dish (60) to cause the metal dish to sit firmly at a tilt.

Figure 11:
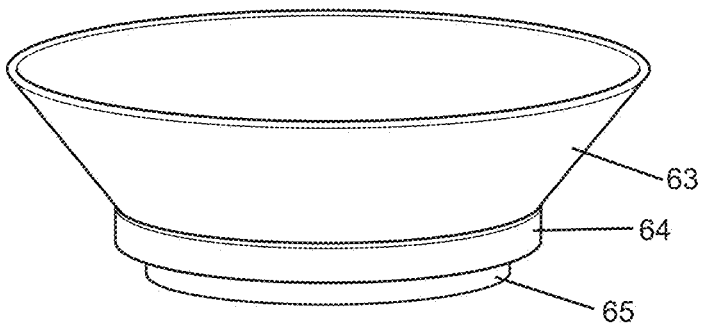
FIG. 11 is a perspective view of a standard metal dish with a standard magnet ring.

FIG. 11 is a perspective side view of a metal dish (63) with a magnet ring (64) surrounding a closed metal base (65).

Figure 12:
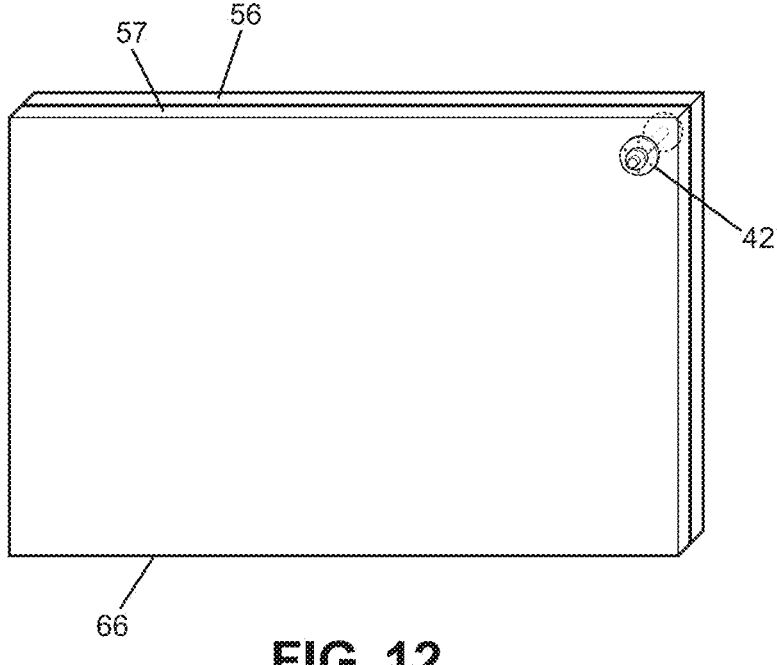
FIG. 12 is a top view of a 2-layer electrostatic grounding mat with a metal male snap for attaching a standard insulated grounding cord.

FIG. 12 is a top view of a standard 2-layer electrostatic grounding mat (66) with a metal male snap mechanism (42) that conductively penetrates all layers of the mat. The mat has an inner electrostatic dissipative layer (56) and an outer carbon infused conductive layer (57). When the device of FIG. 10 (or FIG. 10 with the dish of FIG. 11), is sealed inside and connected to a standard insulated conductive grounding it becomes a very powerful vacuum-like remover of M/EMR within the body, especially important in the brain. A 3-or more layer mat could also be used for increased effectiveness.

Figure 13:
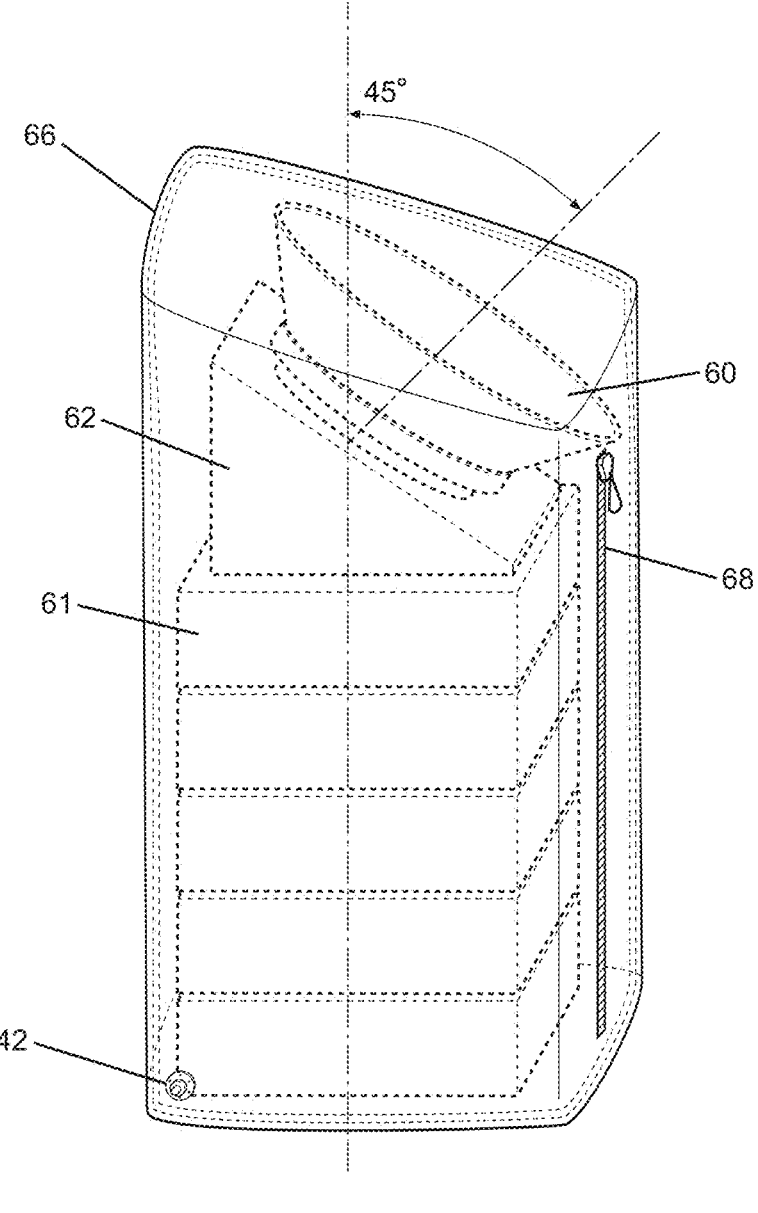
FIG. 13 is a perspective view of the device of FIG. 10, enclosed in the electrostatic grounding mat of FIG. 12.

FIG. 13 is a perspective view of a metal dish (60) magnetically attached to a wedge (62) which is magnetically attached to an N52 magnet body (61) and is enclosed in a 2-layer grounding mat (66) that protects the magnetic device. Also shown is the conductive grounding snap (42). and a zipper (68). The tilted dish provides a comfortable angle to rest the back of the head or the forehead.

Figure 14:
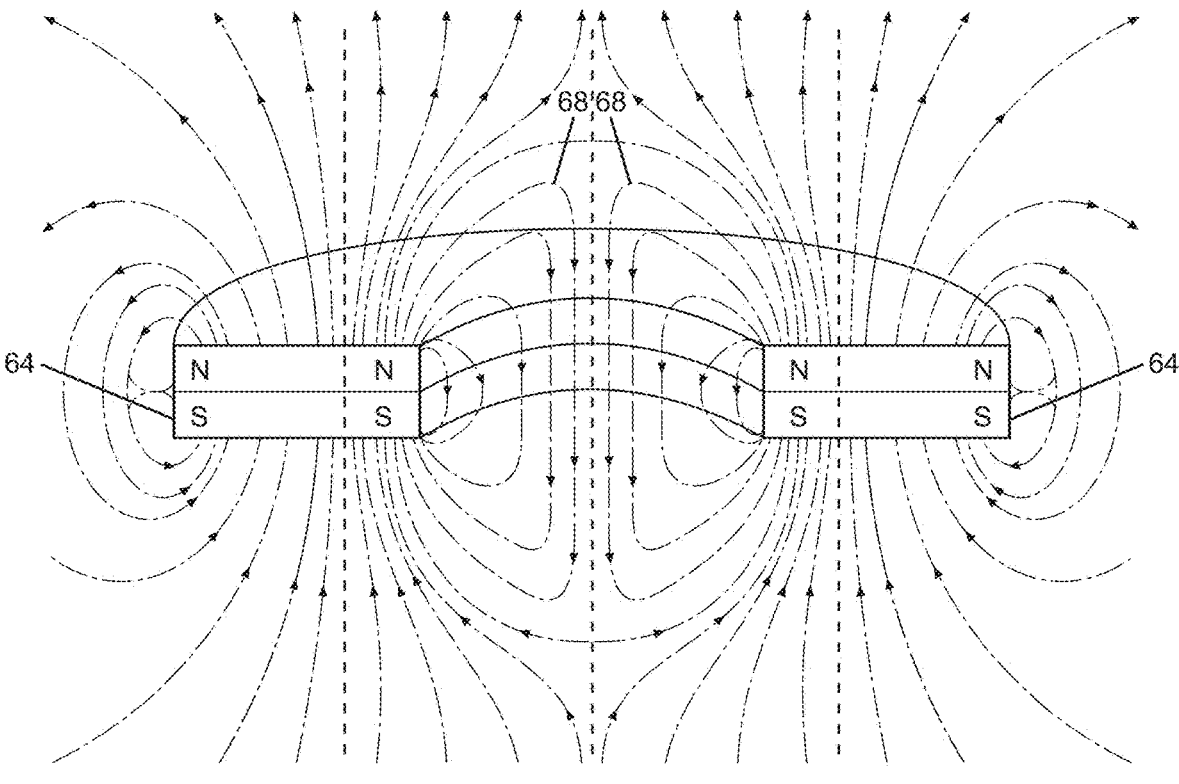
FIG. 14 is a perspective view of the flux lines produced by the magnet ring of FIG. 11.

FIG. 14 is a perspective cross sectional view of a magnet ring (64) that encircles the metal dish of FIG. 11, and the complex flux lines (68) it produces.

Materials contemplated for the handheld assembly include those that can be fabricated from a variety of noncorrosive materials, with some preferred materials being insulative adsorbent PET plastic, a nickel-plated N52 neodymium magnet with an epoxy covering, and distilled water. Grounding cords must be conductive. Grounding mats are contemplated as carbon infused in the conductive layer, and foam polyurethane for the electrostatic dissipative layer. Plastic is contemplated for all insulative layers. Conductive metal is contemplated for the snap mechanisms, conductive grounding cord prongs and wires, dishes that attach to magnets, and the metal base flux plate.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. The invention is not to be limited, except as by the appended claims.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

OTHER PUBLICATIONS

Office of the Director of National Intelligence, News Release No. 1-22, Feb. 2, 2022: "IC Experts Panel on Anomalous Health Incidents (AHIs) DECLASSIFIED by Director of National Intelligence Avril. D. Haines on 1 February," 2022_02_01_AHI_Executive_Summary_FINAL_Redacted.pdf.dni.gov, Washington, D.C.

Edl.Schamiloglu. "Scientists Believe US Embassy Staff and CIA Officers Were Hit with High-Power Microwaves-Here's How the Weapons Work." January, 2021, Edl Schamiloglu is Distinguished Professor of Electrical and Computer Engineering, Associate Dean for Research and Innovation, School of Engineering, University of New Mexico, SciTechDaily.com. Originally published on "The Conversation." *Scientists Believe US Embassy Staff and CIA Officers Were Hit With High-Power Microwaves—Here's How the Weapons Work* (scitechdaily.com)

Williams, K. B., Herb, J. "US Investigating Possible Mysterious Directed Energy Attack Near White House." Apr. 29, 2021, Washington (CNN). http://www.cnn.com/2021/04/29/politics/us-investigating-mysterious-directed-energy-attack-white-house/index.html Kylie Atwood. "CIA Launches Task Force to Probe Invisible Attacks on US Diplomats and Spies as One Victim Finds Some Relief," CNN, Feb. 24, 2021. https://www.cnn.com/2021/02/24/politics/cia-diplomats-sonic-attacks-task-force/index.html.

Jennifer Griffin. "Microwave Weapons are targeting US officials at Home and Abroad," Fox News, May 3, 2021. *Microwave weapons are targeting US officials at home and abroad\Fox News* 60-Minutes," "Havana Syndrome" stumps investigators as U.S. officials report injuries . . . " *"Havana Syndrome" stumps investigators as U.S. officials report injuries on White House grounds•YouTube*

Mizokami, Kyle. "The Air Force Mobilizes Its Laser and Microwave Weapons Abroad," Popular Mechanics, Apr. 9, 2020. *The Air Force Mobilizes Its Laser and Microwave Weapons Abroad—DSIAC* National Academies of Sciences, Engineering, and Medicine. "An Assessment of Illness in U.S. Government Employees and Their Families at Overseas Embassies," Washington, DC. The National Academies Press, 2020. https://doi.org/10.17226/25889.

Help American Victims Afflicted by Neurological Attacks Act of 2021, Public Law 117-4 (10/08/2021), 117th Congress Public Law 46, U.S. Government Publishing Office signed by U.S. President Biden. HAVANA Act of 2021. https://www.congress.gov/bill/117th-congress/senate-bill/1828/text?r=3&s=1 World Health Organization. "IARC Classifies Radiofrequency Electromagnetic Fields as Possibly Carcinogenic to Humans," WHO/International Agency for Research on Cancer, Press Release No. 208, 31 May 2011, Lyon France. *IARC classifies Radiofrequency Electromagnetic Fields as possibly carcinogenic to humans* (who.int)

Keystone Science: "How to Make a Microwave Gun," https://www.bing.com/videos/search?q=youtube+how+to+make+a+microwave+gun&view=detail&mid=7724E204B07AB11CB2107724E204B07AB11CB210&FORM=VIRE Chauhan, P., Verma, H. N., Sisodia, R., Kesari, K. K. "Microwave Radiation (2.45 GHz)—Induced Oxidative Stress: Whole-body exposure effect on histopathology of Wistar Rats," Electromagnetic Biol. Med. 2017; 36(1): 20-30. PMID: 27362544. *Microwave radiation (2.45 GHz)-induced oxidative stress: Whole-body exposure effect on histopathology of Wistar rats·PubMed* (nih.gov)

Matyas Jelinek, Michal Jurajda, Kamil Duris, "Oxidative Stress in the Brain: Basic Concepts and Treatment Strategies in Stroke." Antioxidants (Basel) 2021 Nov. 25; 10(12): 1886. Doi: 10.3390/antiox10121886 PMID: 34942989. *Oxidative Stress in the Brain: Basic Concepts and Treatment Stategies in Stroke—PMC* (nih.gov)

Shcharbina, Natallia, Nechipurenko, Natallia, Matusevich, Ludmila, Anatskaia, Ludmila, "The Antioxidant Effect of Magnesium and Its Protective Role for Blood-Brain Barrier in Acute Stroke—Model and Clinical Studies," Republican Research and Practical Center of Neurology and Neurosurgery, Minsk, Belarus. (*PDF*) *The Antioxidant Effect of Magnesium and Its Protective Role for Blood-Brain Barrier in Acute Stroke·Model and Clinical Studies* (researchgate.net)

Department of Defense Non-Lethal Weapons Program: Intermediate Weapons Capabilities: *Non-Lethal Weapons Program* (defense.gov) and https://jnlwp.defense.gov/Portals/50/Documents/Resources/Publications/Government_Reports/DoD%20 Non-Lethal %20Weapons %20Progrm %20Planning %20Guidance %20March %202020.pdf?ver=2020-05-13-135329-303 and Report on Navy Laser, Railgun and Gun-Launched Guided Projectile>Joint Intermediate Force Capabilities Office>In The News (defense.gov)

Eser, Olcay, et al. "The effect of electromagnetic radiation on the rat brain: an experimental study," PMID 24310452. DOI: 10.5137/1019-5149.JTN.7088-12.2″. *The effect of electromagnetic radiation on the rat brain: an experimental study—PubMed* (nih.gov)

Levallos, P. "Do Power Frequency magnetic Fields Cause Leukemia in Children?" American Journal of Preventive Medicine, July-August 1995; 11(4): 263-270, 1995. *Do power frequency magnetic fields cause leukemia in children?—PubMed* (nih.gov)

Tasalloti, V. "EMF Exposure: Neuropsychiatric Effects," 2021. Neurology, Mar. 11, 2021. *EMF Exposure: Neuropsychiatric Effects—Naturopathic Doctor News and Review* (ndnr.com)

Saygin, Mustafa, et. al. "Impact of 2.45 GHz Microwave Radiation on the Testicular Inflammatory Pathway Biomarkers in Young Rats: The Role of Gallic Acid," Environmental Toxicology, Volume 31, Issue 12, p. 1771-1784.31(12):1771-1784. Doi: 10.1002/tox.22179, Aug. 13, 2015. https://onlinelibrary.wiley.com/doi/10.1002/tox.22179.

Xia, J., Wang, H., Zhang, Q., Zheng, Z., Han, Z. "The Therapeutic Effect of Curcumin in Male Albino Rats and its Putative Mechanisms on Cerebral Microvascular Flow," Brain Research, Volume 1642, 1 Jul., 2016, pp. 131-135. https://doi.org/10.1016/j.brainres.2016.03.022

"Earthing. The Most Important Health Discovery Ever!" © 2014 by Clinton Ober, Stephen T. Sinatra, and M. D., Martin Zucker., Basic Health Publications, Inc. ISBN 978-1-59120-374-2. *Earthing: The Most Important Health Discovery Everl* (*Second Edition*): Ober, Clinton, Sinatra M. D. Dr Stephen T. Zucker. Martin. Oschman Ph.D., James L, Chevalier, Gaetan: 0001591203740: Amazon.com: Books Ober, A. Clinton, "PERSONAL BODY GROUNDING SYSTEM," U.S. Pat. No. 6,683,779 B2. Date of Patent: Jan. 27, 2004. Assignee: Earth Tether International. U.S. Pat. No. 6,683,779B2—Personal body grounding system—Google Patents Ober, A. Clinton, Oschman, James L., "Method of Treating Autoimmune Diseases and Inflammation," U.S. Pat. No. 7,724,491 B2. Date of Patent: May 25, 2010. Assignee: Earth FX, Inc.

Ciechanowski, Dominique, "Magnetotherapy System for Tubs," WO2008/006218 A1. Date of Patent: Jan. 17, 2008.

Chevalier G, Sinatra S T, Oschman, J L, et. al. "Earthing (grounding) the human body reduces blood viscosity: A major factor in cardiovascular disease." Journal of Alternative and Complementary Medicine 2013; 19(2): 102-110; published online at: *Earthing* (*grounding*) *the human body reduces blood viscosity—a major factor in cardiovascular disease*—PubMed (nih.gov)

Oschman, J., Chevalier, G., and Brown, R. "The effects of grounding (earthing) on inflammation, the immune response, wound healing, and prevention and treatment of chronic inflammatory and autoimmune diseases," Journal of Inflammatory Research; 8:83-96, 2015. *The effects of grounding* (*earthing*) *on inflammation, the immune response, wound healing, and prevention and treatment of chronic inflammatory and autoimmune diseases*—PubMed (nih.gov)

H. L. Bansal, "Magnetotherapy: The Art of Healing Through Magnets," Published 1976 by B. Jain Publishers New Delhi. *How Magnetic Therapy Works—ProMagnet*

Kong, S. D. et. al. "Magnetic Targeting of Nanoparticles Across the Intact Blood Brain Barrier," Journal Control Release; 164(1)" 49-57, Nov. 28, 2012 *Magnetic targeting of nanoparticles across the intact blood—brain barrier—PMC* (nih.gov)

Mayo Clinic. "Transcranial Magnetic Stimulation," November, 2018. https://www.mayoclinic.org/tests-procedured/transcranial-magnetic-stimulation/about/pac-20384625

Environment, Health, and Safety, 2018 Electromagnetic Radiation and Fields (lbl.gov) NIMH, National Institute of Mental Health, National Institutes of Health. nimh.nih.gov. "Brain Stimulation Therapies." https://www.nimh.nih.gov/health/topics/brain-stimulation-therapies/brain-stimulation-therapies Roland, J. "E-Stim. What it is, How it Works, and Why it May Help You. Is E-Stim the Answer to Your Pain?" Healthline, Jul. 29, 2019. *E-Stim: What It Is, How It Works, and Why It May Help You* (healthline.com)

Eccles, Nyjon. "A Critical Review of Randomized Controlled Trials of Static Magnets for Pain Relief," K., Journal of Alternative Complementary Medicine; 11 (3):

495-509. Doi: 10.1089/acm.2005.11.495. PMID: 15992236, June 2005. https://pubmed.ncbi.nlm.nih.gov/15992236/

QMagnets. "Magnetic Therapy.": https://qmagnets.com/magnetic-therapy/

QMagnets. "New Research Paper Explores How Magnets May Relieve Pain . . . " Magnetic Therapy, Popular, Research, Feb. 25, 2017. *Q Magnets* by Neuromagnetics Australia Sorokina, N. D., Pertsov, S. S., Selitsky, G. V., I. P. Pavlov. "Neurobiological mechanisms of transcranial magnetic stimulation and its comparative efficacy in tension headache and migraine," Russian Medical Biological Herald, Vol. 26, No. 3 (2018), pp 417-429. *Neurobiological mechanisms of transcranial magnetic stimulation and its comparative efficacy in tension headache and migraine—Sorokina—I. P. Pavlov Russian Medical Biological Herald* (eco-vector.com)

I claim:

1. A personal multi-component portable grounding system to repel or collect and remove electromagnetic radiation and excess electrical and magnetic fields from a human brain and body, comprised of:

a non-electrically conductive insulating plastic container for repelling excess electrical current directed into or ambiently toward nearby body tissue when worn on or near said human brain and body having a central body with a top end and a bottom end;

said central body having an inside and an outside;

said central body top end being open;

said central body bottom end being closed;

said central body containing at least one bar magnet for attracting excess magnetic field unto itself from already inside said human brain and body and from that being directed into the human brain and body in real-time;

each bar magnet having four elongated length sides and two width ends is diametrically magnetized;

said central body being configured at its top end to accept and hold secure a cap for retaining said at least one diametrically magnetized bar magnet within said central body inside;

said cap having a closed top end and an open bottom end and being capable of being securely connected to said central body open top end;

said central body open top end capable of connecting securely to said cap open bottom end;

said cap being made of non-electrically conductive plastic for repelling electrical current, wherein:

said central body inside containing said at least one diametrically magnetized bar magnet and being sealed closed by said cap; and said central body with said cap and said at least one diametrically magnetized bar magnet is duplicated and each said central body with said cap and said at least one diametrically magnetized bar magnet each then being connected together by magnetism along their respective said elongated length sides, thus forming a stable and laborious to separate side-by-side device duo functioning now as a single magnet with fixed flux conditions after having accomplished a polarity shift to the exposed unattached said elongated length sides for use according to therapeutic needs and preferences when placed on or near said human brain and body, and for causing consistent alignment of cellular-level magnetic field polarity orientations to promote increasingly faster electromagnetic radiation removal over time with a stability aided by the now broadened planar surface of said combined central bodies.

2. The system of claim 1, further comprising:

said at least two diametrically magnetized magnets are rare earth N52 magnets, the strongest available, for drawing out a maximum amount of magnetic field from a maximum depth for its size from a said human brain and body;

said at least two magnets having an interior and exterior;

said at least two magnets each having an exterior consisting of at least one protective coating;

said protective coatings being water-resistant or water-proof; and said central bodies now being filled with water to further disable the ability of any electrical current to reach said magnets or nearby body tissue and to serve as a warning system if small bubbles begin to appear along any container walls in said central bodies insides due to "water-splitting".

3. The system of claim 2, further comprising:

said device duo having at least one of said caps having a port on its closed top end;

said water is distilled water;

said port having a rubber stopper to prevent any outflow of said distilled water when held in any position in space during use or in travel when said cap is secured to said central body top end;

a standard insulated conductive grounding cord having a first end and a second end;

a metal prong conductively connected to said standard insulated grounding cord first end and being capable of being inserted securely through said rubber stopper for device portability or inserted into a grounding hole of a properly grounded electrical outlet;

a standard conductive female snap mechanism end conductively connected to said grounding cord second end and configured to connect to standard conductive grounding equipment for grounding portability comprising a conductive grounding mat, or patch or band for removal of excess electrical, magnetic, or electro-magnetic currents from said human brain and body.

4. The system of claim 3, wherein:

said conductive grounding mat is single-layer having edges all the way around it and said at least one magnet rolled up in or otherwise secured along said edges; and said single-layer conductive grounding mat being conductively penetrated by a standard conductive male snap and capable of connecting conductively to said device duo by said female snap mechanism with said grounding cord.

5. The system of claim 4, wherein:

said single-layer conductive grounding mat with said edges being duplicated wherein the two single-layer mats are secured together along said edges and said at least one magnet is embedded and secured in between said two single-layer mats; and said duplicated single-layer conductive grounding mats with said at least one magnet secured within being conductively penetrated by a standard conductive male snap and capable of connecting conductively to said device duo by said female snap mechanism with said grounding cord.

6. The system of claim 5, further comprising:

said at least one magnet being attached magnetically to a shallow metal dish, wherein:

said metal dish having an inside and an outside and an open topside and a closed bottom side;

said metal dish being connected by magnetism to said at least one magnet at it's said closed bottom side;

said standard conductive grounding mat having two layers, an inner layer and an outer layer and being wrapped and sealed securely around said at least one magnet and said dish being bound at its outer edges such that the grounding mat bottom inner layer touches said at least one magnet and said metal dish and no portion of said bottom inner layer is externally exposed; and said standard conductive grounding mat said inner layer and said conductive grounding mat outer layer being conductively penetrated by a male snap mechanism for connecting, with said female snap mechanism.

7. The system of claim 6, further comprising:

a magnetic band encircling said metal dish at its closed bottom side.

8. The system of claim 7, further comprising:

a wedge-shaped metal object;

said wedge having a narrow end and a wide end; and said wedge narrow end being capable of fitting in between said metal dish and said at least one magnet for causing said metal dish to tilt.

9. The system of claim 6, further comprising:

a wedge-shaped metal object;

said wedge having a narrow end and a wide end; and said wedge narrow end being capable of fitting in between said metal dish and said at least one magnet for causing said dish to tilt.

10. The system of claim 3, wherein:

said conductive grounding mat is a two-layer conductive grounding mat having a top end and a bottom end, a left side and a right side, an upper right-side edge and a lower right-side edge, an upper left side edge and a lower left side edge, an upper left side and an upper right side, a top layer, a bottom layer, and outer edges;

said top layer being included of including a conductive material; such as being comprised of a carbon infused material;

said bottom being comprised of an electrostatic dissipative material; and said top layer and said bottom layer being conductively penetrated by a standard conductive male snap;

said standard two-layer conductive grounding mat is duplicated and the two said conductive grounding mats are attached to one another by their respective said electrostatic dissipative material said bottom layers to form an electrostatic dissipative material center and bound at said outer edges to form a single non-standard conductive grounding mat with a middle layer comprised of said electrostatic dissipative material center with said a conductive layer comprising two outer layers, further comprising:

said top layer, material center, and outer layer of said non-standard conductive grounding mat being penetrated by a conductive male snap mechanism;

said top layer, material center, and outer layer being connected along their outer edges such that no portion of said center layer is exposed for enabling attraction of electricity to said dissipative material center from inside said human brain and body rather than from accumulating from ambient environmental electrical field which would pre-saturate said middle layer and slow removal of electricity from said human brain and body;

a standard insulated conductive grounding cord having a first end and a second end;

said metal prong conductively connected to said grounding cord first end and being capable of being inserted securely through said port into said distilled water and being free-floating or magnetically connected to said at least two magnets and said prong also being capable of fitting securely into a grounding hole of a properly grounded electrical outlet; and said conductive grounding cord second end configured to connect said conductive male snap mechanism on said non-standard or said standard one- or two-layer conductive grounding mats to thereby divert excess electrical and magnetic field away from said human brain and body and into said non-standard or said standard one- or two-layer grounding mats via said conductive grounding cord and direct any excess magnetic or electric or electromagnetic fields into at least one central body of said device duo or into a grounding hole of a properly grounded electrical outlet.

11. The system of claim 10, further comprising:

one or more magnets inserted and orientationally north pole-south pole secured in between said top and bottom layers of said non-standard conductive grounding, mat for providing superior ability of said non-standard conductive grounding mat to draw out excess electric, plus magnetic, or electromagnetic fields from said human brain and body and for aligning cellular-level magnetic field orientation for increasingly faster removal over time.

12. The system of claim 10, wherein the non-standard grounding mat comprises:

an upper fold to create an upper closable flap and a lower fold to create a carrying case for portability of said device duo; and said left side edges being partly sewn or otherwise secured together and said right side edges being partly sewn or otherwise secured together to enable said device duo to be securely and freely transported.

13. The system of claim 12, further comprising:

an upper right side and an upper left side of said non-standard grounding mat, each having a strap sewn or otherwise connected to it;

said upper right side strap having a near end and a far end;

said upper left side strap having a near end and a far end; and said upper right and upper left side straps being connectable to one another at their far ends by a male clasp mechanism and a female clasp mechanism respectively and connected to said non-standard grounding mat at their respective near ends.

14. The system of claim 12, further comprising:

a protective covering for repelling focused streams of electromagnetic radiation, said covering comprising:

a bottom layer with a top side and a bottom side, a middle layer with a top side and a bottom side, and a top layer with a top side and a bottom side;

said bottom layer being composed of a non-conductive flexible plastic;

said middle layer being composed of Biaxially-oriented polyethylene terephthalate (BoPET) for preventing rays of electromagnetic magnetic radiation from passing through it and being adhesively affixed to said bottom layer top side and to said top layer bottom side;

said top layer being composed of a non-conductive flexible polyethylene terepthalate (PET) plastic material adhesively affixed to said middle layer top side; and said protective covering being configured to fit into said carrying case for transport.

15. The device of claim 14, further comprising:

said bottom layer bottom side having a light skin-friendly adhesive for making said protective covering into a patch.

16. The system of claim 3, further comprising:

another said central body with said cap containing said at least one magnet;

wherein said device duo is supplemented by attaching by magnetics to the another said central body with said cap containing said at least one magnet and filled with said distilled water to form a device trio for broadening and deepening a natural magnetic reach of said device duo into said human brain and body by adding strength and complexity to flux fields.

17. The system of claim 2, further comprising:

another said central body with said cap containing said at least one magnet;

wherein said device duo is supplemented by attaching by magnetics to the another said central body with said cap containing said at least one magnet and filled with said distilled water to form a device trio for broadening, and deepening a natural magnetic reach of said device duo into said human brain and body by adding strength and complexity to flux fields.

18. The system of claim 1, further comprising:

another said central body with said cap containing said at least one magnet;

wherein said device duo is supplemented by attaching by magnetics to the another said central body with said cap containing said at least one magnet to form a device trio for broadening and deepening a natural magnetic reach of said device duo into said human brain and body by adding strength and complexity to flux fields.

* * * * *